(12) United States Patent
Mann et al.

(10) Patent No.: US 9,610,234 B2
(45) Date of Patent: *Apr. 4, 2017

(54) COMBINATIONS OF ALKYLAMIDOTHIAZOLES AND PRESERVATIVES

(71) Applicant: Beiersdorf AG, Hamburg (DE)

(72) Inventors: Tobias Mann, Hamburg (DE); Cathrin Scherner, Norderstedt (DE); Ludger Kolbe, Dohren (DE); Jan Batzer, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/774,100

(22) PCT Filed: Feb. 14, 2014

(86) PCT No.: PCT/EP2014/052968
§ 371 (c)(1),
(2) Date: Sep. 9, 2015

(87) PCT Pub. No.: WO2014/139757
PCT Pub. Date: Sep. 18, 2014

(65) Prior Publication Data
US 2016/0015615 A1   Jan. 21, 2016

(30) Foreign Application Priority Data
Mar. 11, 2013 (DE) .......... 10 2013 204 081

(51) Int. Cl.
| | | |
|---|---|---|
| A61K 8/49 | (2006.01) | |
| A61K 8/34 | (2006.01) | |
| A61K 8/36 | (2006.01) | |
| A61K 8/368 | (2006.01) | |
| A61K 8/37 | (2006.01) | |
| A61K 8/40 | (2006.01) | |
| A61K 8/41 | (2006.01) | |
| A61K 8/44 | (2006.01) | |
| A61Q 19/02 | (2006.01) | |
| A61K 8/42 | (2006.01) | |
| A61Q 5/00 | (2006.01) | |
| A61Q 5/02 | (2006.01) | |
| A61Q 5/12 | (2006.01) | |

(52) U.S. Cl.
CPC ............... *A61K 8/494* (2013.01); *A61K 8/34* (2013.01); *A61K 8/345* (2013.01); *A61K 8/36* (2013.01); *A61K 8/368* (2013.01); *A61K 8/37* (2013.01); *A61K 8/375* (2013.01); *A61K 8/40* (2013.01); *A61K 8/416* (2013.01); *A61K 8/42* (2013.01); *A61K 8/44* (2013.01); *A61K 8/49* (2013.01); *A61K 8/4906* (2013.01); *A61K 8/498* (2013.01); *A61K 8/4926* (2013.01); *A61K 8/4946* (2013.01); *A61Q 19/02* (2013.01); *A61K 2800/524* (2013.01); *A61K 2800/591* (2013.01); *A61Q 5/006* (2013.01); *A61Q 5/02* (2013.01); *A61Q 5/12* (2013.01)

(58) Field of Classification Search
CPC ...... A61K 8/34; A61K 2800/591; A61K 8/36; A61K 8/368
USPC ............................................ 424/62; 514/371
See application file for complete search history.

(56) References Cited

U.S. PATENT DOCUMENTS

| | | | | |
|---|---|---|---|---|
| 6,956,062 | B2 * | 10/2005 | Beilfuss | A61K 8/345 514/458 |
| 8,211,412 | B2 | 7/2012 | Hanyu et al. | |
| 8,324,234 | B2 | 12/2012 | Hanyu et al. | |
| 8,426,435 | B2 | 4/2013 | Hanyu et al. | |
| 8,563,552 | B2 | 10/2013 | Hanyu et al. | |
| 8,920,785 | B2 | 12/2014 | Kolbe et al. | |
| 2004/0224992 | A1 * | 11/2004 | Cywin | C07C 235/38 514/357 |
| 2009/0233975 | A1 * | 9/2009 | Suetsugu | A61K 8/49 514/371 |
| 2010/0316584 | A1 | 12/2010 | Hanyu et al. | |
| 2010/0324096 | A1 | 12/2010 | Hanyu et al. | |
| 2011/0003817 | A1 | 1/2011 | Hanyu et al. | |
| 2012/0134944 | A1 | 5/2012 | Hanyu et al. | |
| 2013/0039870 | A1 | 2/2013 | Kolbe et al. | |
| 2013/0045173 | A1 | 2/2013 | Hanyu et al. | |
| 2014/0121250 | A1 * | 5/2014 | Kolbe | C07D 277/48 514/371 |

FOREIGN PATENT DOCUMENTS

| | | | |
|---|---|---|---|
| DE | 102011083259 | * | 3/2013 |
| EP | 1911750 A1 | | 4/2008 |
| WO | 2009099195 A1 | | 8/2009 |
| WO | 2011117034 A2 | * | 9/2011 |
| WO | 2013041526 A1 | | 3/2013 |
| WO | 2013041535 A1 | | 3/2013 |
| WO | 2013041537 A1 | | 3/2013 |

OTHER PUBLICATIONS

Leschke; title: Ehtylhexylglycerin for a improved skin feel; SOFW Journal, vol. 136, pp. 10-14, published Aug. 2010.*
J. P. Germanas et al., Bioorg. Med. Chem. Lett. 17 (2007) 6871-6875.
M. Seiberg et al., 2000, J. Cell. Sci., 113:3093-101.
A.M. Kligman et al., Arch. Dermatol. 1975 vol. 111, pp. 40-48.

* cited by examiner

*Primary Examiner* — Yanzhi Zhang
(74) *Attorney, Agent, or Firm* — Abel Law Group, LLP

(57) ABSTRACT

Disclosed are active ingredient combinations of alkylamidothiazoles and one or more cosmetically or dermatologically acceptable preservatives.

20 Claims, No Drawings

COMBINATIONS OF ALKYLAMIDOTHIAZOLES AND PRESERVATIVES

BACKGROUND OF THE INVENTION

1. Field of the Invention

The present invention relates to active ingredient combinations of alkylamidothiazoles and one or more cosmetically or dermatologically acceptable preservatives. Furthermore, the present invention relates to cosmetic or dermatological preparations with a content of such active ingredient combinations, and to the use thereof for lightening human skin.

2. Discussion of Background Information

Melanocytes are responsible for the pigmenting of the skin; these are found in the lowest layer of the epidermis, the Stratum basale, alongside the basal cells as pigment-forming cells which, depending on the skin type, occur either individually or in clusters of varying size.

Melanocytes contain, as characteristic cell organelles, melanosomes, in which the melanin is formed. Inter alia, upon stimulation by UV radiation, melanin is formed to a greater extent. This is transported via the living layers of the epidermis (keratinocytes) ultimately into the horny layer (corneocytes) and brings about a more or less pronounced brownish to brown-black skin color.

Melanin is formed as the end stage of an oxidative process in which tyrosine is converted, under the co-action of the enzyme tyrosinase, via several intermediates, to the brown to brown-black eumelanins (DHICA and DHI melanin), or, with the participation of sulfur-containing compounds, to the reddish pheomelanin. DHICA and DHI melanin are formed via the common intermediates dopaquinone and dopachrome. The latter, sometimes with the participation of further enzymes, is converted either to indole-5,6-quinonecarboxylic acid or into indole-5,6-quinone, from which the two specified eumelanins are formed.

The formation of pheomelanin proceeds inter alia via the intermediates dopaquinone and cysteinyldopa. The expression of the melanin-synthesizing enzymes is controlled by a specific transcription factor (microphthalmia-associated transcription factor, MITF). Besides the described enzymatic processes of the melanin synthesis, further proteins are also of importance for the melanogenesis in the melanosomes. An important role here appears to be attributed to the so-called p-protein, although the exact function is still unclear.

As well as the above-described process of the melanin synthesis in the melanocytes, the transfer of the melanosomes, their stay in the epidermis and also their degradation and the degradation of the melanin are also of decisive importance for the pigmenting of the skin. It was shown that the PAR-2 receptor is important for the transport of the melanosomes from the melanocytes into the keratinocytes (M. Seiberg et al., 2000, J. Cell. Sci., 113:3093-101).

In addition, size and shape of the melanosomes have an influence on their light-scattering properties and thus the color appearance of the skin. For example, in black Africans there are more large spheroidal individual melanosomes, whereas in Caucasians, smaller melanosomes occurring in groups are to be found.

Problems with hyperpigmentation of the skin have a wide variety of causes and/or are accompanying phenomena of many biological processes, e.g. UV radiation (e.g. freckles, Ephelides), genetic disposition, incorrect pigmentation of the skin during wound healing or scarring (post-inflammatory hyperpigmentation) or skin aging (e.g. Lentigines seniles).

After inflammatory reactions, the pigmentation system of the skin reacts with sometimes opposite reactions. This can lead either to post-inflammatory hyperpigmentations or hypopigmentations. Post-inflammatory hypomelanoses often arise inter alia in conjunction with atopy, Lupus erythematosus and psoriasis. The different reaction forms of the pigmentation system of the human skin as a result of inflammatory phenomena are understood only very incompletely.

Problems with post-inflammatory hyperpigmentation often occur in darker skin types. Particularly in colored males, the problem of Pseudofollikulitis barbae is known, which is associated with cosmetically undesired incorrect pigmentation and/or leads to this. Forms of melasma, which occur in particular in women of Asiatic origin on the face and on the decolletage area, and also various forms of irregular pigmentation of the skin are also types of post-inflammatory hyperpigmentations. In addition, dark circles around the eyes are also considered to be a form of post-inflammatory hyperpigmentations, the underlying inflammation in most cases proceeding without clinical manifestations.

In many cases, post-inflammatory incorrect pigmentations of this type are increased further by the action of sunlight (UV light) without resulting in a UV-induced inflammation (sunburn).

Active ingredients and preparations are known which counteract skin pigmentation. In practical use these are essentially preparations based on hydroquinone, although, on the one hand, these only exhibit their effect after application for several weeks, and, on the other hand, their excessively long application is unacceptable for toxicological reasons. Albert Kligman et al. have developed a so-called "triformula" which constitutes a combination of 0.1% tretinoin, 5.0% hydroquinone, 0.1% dexamethasone (A. Kligman, 1975, Arch. Dermatol., 111:40-48). However, this formulation too is highly disputed on account of possible irreversible changes in the pigmentation system of the skin.

In addition, skin-peeling methods (chemical and mechanical "peels") are used, although these often lead to inflammatory reactions and, on account of post-inflammatory hyperpigmentations which may subsequently arise, can even lead to greater pigmentation instead of reduced pigmentation. All of these customary methods, which are also used for treating post-inflammatory hyperpigmentations, are characterized by distinct side effects.

Furthermore, various other substances are known for which a skin-lightening effectiveness is described. Mention is to be made here inter alia of hexadecene-1,16-dicarboxylic acid, kojic acid and derivatives, arbutin, ascorbic acid and derivatives, flavonoids, ellagic acid and derivatives, tranexamic acid and various resorcinol derivatives, such as e.g. 4-n-butylresorcinol, 4-n-hexylresorcinol and 4-(1-phenylethyl)benzene-1,3-diol.

J. M. Ready describes in a publication (Bioorganic & Medicinal Chemistry Letter 17 (2007) 6871-6875) the effect of inter alia substituted thiazole derivatives for the inhibition of Mush-room tyrosinase.

The patent application from Shiseido (WO 2009/099195) describes substituted thiazolamines and hydrothiazolamines for lightening skin.

The substances described in the aforementioned prior art are proven by a moderate effectiveness.

Rings around the eyes can likewise be formed as a result of a pigmentation disorder, with them in addition also appearing as a reaction to general stress, such as e.g. too little sleep or simply as a result of overexerting the eyes. In younger people, the symptoms disappear again after an adequate nighttime rest, but, over prolonged periods, the condition can become chronic and very troublesome for those affected. There is also a lack of sufficiently promising active ingredients and treatment options to combat such skin phenomena.

It was therefore an aim of the invention below to provide a remedy for the disadvantageous prior art.

SUMMARY OF THE INVENTION

This object is achieved by active ingredient combinations of alkylamidothiazoles and one or more cosmetically or dermatologically acceptable preservatives.

Advantageous embodiments of the present invention are also cosmetic or dermatological preparations with a content of such active ingredient combination, and the use thereof for lightening human skin.

Advantageously, preparations according to the invention comprise one or more preservatives, where the total amount of the preservatives is e.g. 0.00001% by weight to 10% by weight, preferably 0.001% by weight-5% by weight, in particular 0.005% by weight-3% by weight, based on the total weight of the preparations, in order to provide cosmetic preparations.

In the context of the present invention, advantageous preservatives are ethylparaben (120-47-80), propylparaben (94-13-3), methylisothiazolinone (2682-20-4), methylpropanediol (2163-42-0), butylene glycol (107-88-0), propylene glycol (57-55-6, 4254-14-2, 4254-15-3), ethylhexyl-glycerol (70445-33-9), sodium benzoate (532-32-1), 1,2-hexanediol (6920-22-5), 1,3-butanediol (107-88-0), 1,2-octanediol (1117-86-8), potassium sorbate (24634-61-5/590-00-1), DMDM hydantoin (6440-58-0), benzyl alcohol (100-51-6), phenoxyethanol (122-99-6), dehydroacetic acid (520-45-6), piroctone olamine (68890-66-4), methylparaben (99-76-3), alcohol (64-17-5), octanehydroxamic acid (7377-03-9), benzethonium chloride (121-54-0), glyceryl caprylate (26402-26-6), pentylene glycol (111-29-5), lauroyl ethyl arginate (60372-77-2), salicylic acid (69-72-7), benzoic acid (65-85-0), propionic acid (79-09-4), sorbic acid (110-44-1), where salicylic acid, benzoic acid and dehydroacetic acid are preferred and it may also be advantageous to use physiologically acceptable water-soluble metal salts of these acids.

Preferred preservatives are: methylisothiazolinone (2682-20-4), potassium sorbate (24634-61-5/590-00-1), sodium benzoate (532-32-1), ethylhexylglycerol (70445-33-9), benzyl alcohol (100-51-6), benzethonium chloride (121-54-0), salicylic acid (69-72-7), benzoic acid (65-85-0), propionic acid (79-09-4), sorbic acid (110-44-1).

Preferably, the preparations according to the invention comprise 0.0001-10% by weight of one or more preservatives, preferably 0.001-5% by weight of one or more preservatives, particularly preferably 0.005-3% by weight of one or more preservatives.

Of advantage are in particular preparations or uses according to the invention, characterized in that the preparations comprise 0.000001 to 10% by weight, in particular 0.0001 to 3% by weight, very particularly 0.001 to 1% by weight of one or more alkylamidothiazoles, based on the total weight of the composition.

Advantageous alkylamidothiazoles in the context of the present invention are substances of the general formula

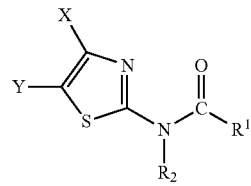

in which
$R^1$, $R^2$, X and Y can be different, partly identical or completely identical and, independently of one another, can mean:
$R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alky-morpholino, —$C_1$-$C_{24}$ alky-piperidino, —$C_1$-$C_{24}$ alky-piperazino, —$C_1$-$C_{24}$ alky-piperazino-N-alkyl,
$R_2$=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-hydroxyalkyl (linear and branched), —$C_1$-$C_{24}$-alkylaryl (linear and branched), —$C_1$-$C_{24}$-alkylheteroaryl (linear and branched),
X=—H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl (optionally mono- or polysubstituted with —OH, —F, —Cl, —Br, —I, —OMe, —$NH_2$, —CN), —$C_1$-$C_{24}$-heteroaryl (optionally mono- or polysubstituted with —OH, —F, —Cl, —Br, —I, —OMe, —$NH_2$, —CN), —$C_1$-$C_{24}$-alkylaryl (linear and branched), —$C_1$-$C_{24}$-alkylheteroaryl (linear and branched), -aryl (optionally mono- or polysubstituted with —OH, —F, —Cl, —Br, —I, —OMe, —$NH_2$, —CN), -phenyl, -2,4-dihydroxyphenyl, -2,3-dihydroxyphenyl, -2,4-dimethoxyphenyl, -2,3-dimethoxyphenyl,
Y=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cycloalkyl, —COO-aryl, —COO-heteroaryl,
and X, Y can optionally also=condensed aromatic,
where X and Y can form with one another aromatic or aliphatic homo- or heterocyclic ring systems with up to n ring-forming atoms, and where the number n can assume values from 5 to 8, and the respective ring systems can in turn be substituted with up to n–1 alkyl groups, hydroxyl groups, carboxyl groups, amino groups, nitrile functions, sulfur-containing substituents, ester groups and/or ether groups.

Said thiazoles can either be in the form of the free base or the salt: e.g. fluoride, chloride, bromide, iodide, sulfate, carbonate, ascorbate, acetate or phosphate. In particular in the form of halogen salts, such as e.g. chloride and bromide.

Furthermore, there is an advantageous realization of the present invention in cosmetic or dermatological preparations with an effective content of one or more aforementioned alkylamidothiazoles.

Also in accordance with the invention is the use of the aforementioned alkylamidothiazoles for the treatment and/or prophylaxis of undesired skin pigmentation.

Here, treatment and/or prophylaxis of undesired skin pigmentation can be both in the cosmetic sphere and in the pharmaceutical sphere.

In this connection, the pharmaceutical (or dermatological) treatment is primarily understood for diseased skin conditions, whereas the cosmetic treatment and/or prophylaxis of undesired skin pigmentation primarily relates to healthy skin.

Advantageously, X is selected from the group of substituted phenyls, in which case the substituents (Z) can be selected from the group —H, —OH, —F, —Cl, —Br, —I, —OMe, —NH$_2$, —CN, acetyl and can be identical or different.

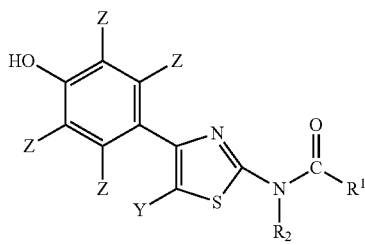

Particularly advantageously, X is selected from the group of phenyl groups substituted with one or more hydroxy groups, in which case the substituent (Z) can be selected from the group —H, —OH, —F, —Cl, —Br, —I, —OMe, —NH$_2$, —CN, acetyl, and preference is given to the following generic structure in which Y, $R^1$ and $R^2$ can have the properties defined above.

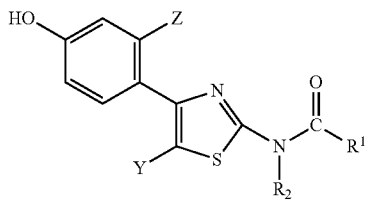

Particularly advantageous compounds are those in which

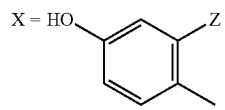

Y=H
$R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$ alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alky-morpholino, —$C_1$-$C_{24}$ alky-piperidino, —$C_1$-$C_{24}$ alky-piperazino, —$C_1$-$C_{24}$ alky-piperazino-N-alkyl,
$R_2$=H, —$C_1$-$C_{24}$-alkyl (linear and branched),
Z=—H, —OH, —F, —Cl, —Br, —I, —OMe, —NH$_2$, —CN, acetyl.

Particular preference is given to those compounds in which

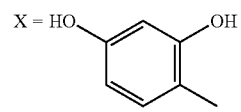

Y=H
$R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alky-morpholino, —$C_1$-$C_{24}$ alky-piperidino, —$C_1$-$C_{24}$ alky-piperazino, —$C_1$-$C_{24}$ alky-piperazino-N-alkyl,
$R_2$=H.

The compounds

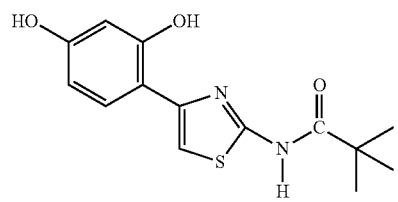 [SMILES: CC(C)(C)C(=O)Nc1nc(-c2ccc(O)cc2O)cs1]

N-(4-(2,4-dihydroxyphenyl)thiazol-2-yl)pivalamide

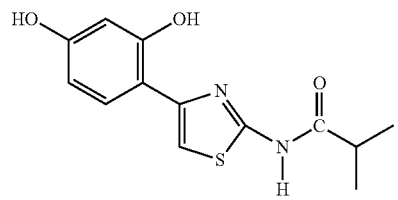 [SMILES: CC(C)C(=O)Nc1nc(-c2ccc(O)cc2O)cs1]

N-(4-(2,4-dihydroxyphenyl)thiazol-2-yl)isobutyramide

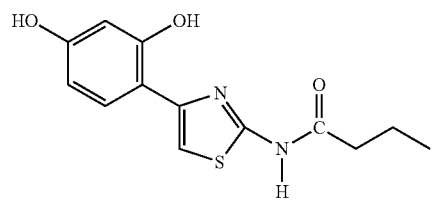 [SMILES: CCCC(=O)Nc1nc(-c2ccc(O)cc2O)cs1]

N-(4-(2,4-dihydroxyphenyl)thiazol-2-yl)butyramide

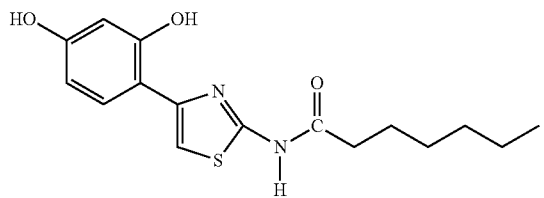 [SMILES: CCCCCCC(=O)Nc1nc(-c2ccc(O)cc2O)cs1]

N-(4-(2,4-dihydroxyphenyl)thiazol-2-yl)heptanamide

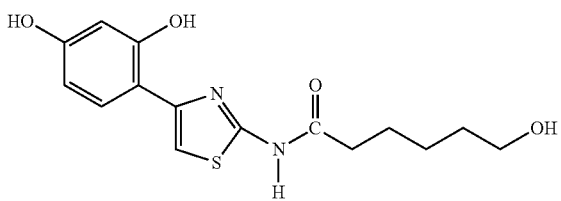 [SMILES: O=C(CCCCCO)Nc1nc(-c2ccc(O)cc2O)cs1]

N-(4-(2,4-dihydroxyphenyl)thiazol-2-yl)-6-hydroxyhexanamide

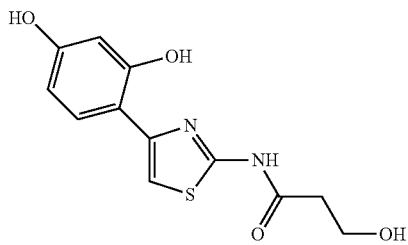 [SMILES: O=C(CCO)Nc1nc(-c2ccc(O)cc2O)cs1]

N-(4-(2,4-dihydroxyphenyl)thiazol-2-yl)-3-hydroxypropanamide

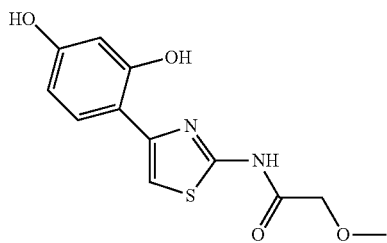 [SMILES: COCC(=O)Nc1nc(-c2ccc(O)cc2O)cs1]

N-(4-(2,4-dihydroxyphenyl)thiazol-2-yl)-2-methoxyacetamide

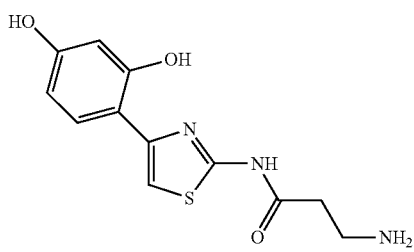 [SMILES: NCCC(=O)Nc1nc(-c2ccc(O)cc2O)cs1]

3-amino-N-(4-(2,4-dihydroxyphenyl)thiazol-2-yl)propanamide

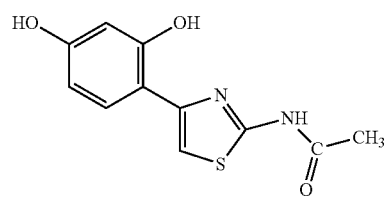 [SMILES: CC(=O)Nc1nc(-c2ccc(O)cc2O)cs1]

N-(4-(2,4-dihydroxyphenyl)thiazol-2-yl)acetamide

N-(4-(2,4-dihydroxyphenyl)thiazol-2-yl)-4-(hydroxymethyl)cyclohexanecarboxamide

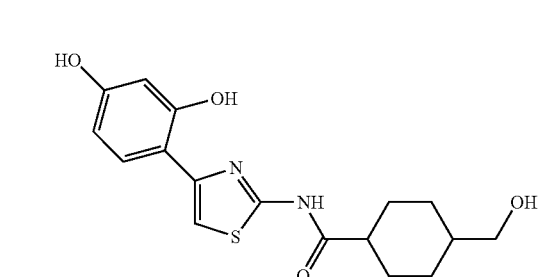

N-(4-(2,4-dihydroxyphenyl)thiazol-2-yl)cyclohexanecarboxamide
and

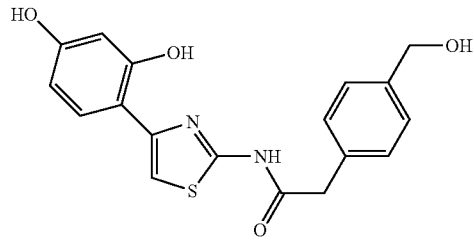 [SMILES: O=C(Cc1ccc(CO)cc1)Nc1nc(-c2ccc(O)cc2O)cs1]

N-(4-(2,4-dihydroxyphenyl)thiazol-2-yl)-2-(4-(hydroxymethyl)phenyl)acetamide
are preferred according to the invention.

Surprisingly, it was possible to show that the alkylamidothiazoles according to the invention in combination with UV filters according to the invention have an increased effectiveness.

Method Description of the Effectiveness Investigations:

The effectiveness of the thiazoles was demonstrated using an enzyme test in which conversion of L-DOPA to L-dopaquinone by a human tyrosinase was measured. In this literature-known method (Winder, A. J. and Harris, H., New assays for the tyrosine hydroxylase and dopa oxidase activities of tyrosinase. Eur. J. Biochem. (1991), 198, 317-26), the reaction product L-dopaquinone is reacted with MBTH (3-methyl-2-benzothiazoline hydrazone) to give a pink-colored substance, the increase of which is measured over time by absorption at 490 nm. Table 1 shows by way of example effectiveness data for some of the claimed substances. It can be concluded from this that the substances according to the invention are extremely effective pigmentation-inhibiting substances.

TABLE

Inhibition of the tyrosinase activity by the combination of N-(4-(2,4-dihydroxyphenyl)thiazol-2-yl)isobutyramide with various preservatives

| Substance | Inhibition (% of the control) | Concentration |
|---|---|---|
| N-(4-(2,4-Dihydroxyphenyl)thiazol-2-yl)isobutyramide | 38.2 | 0.4 µg/mL |
| Sodium benzoate | 43.6 | 200 µg/mL |
| N-(4-(2,4-Dihydroxyphenyl)thiazol-2-yl)isobutyramide + sodium benzoate | 58.0 | 200.4 µg/mL |
| N-(4-(2,4-Dihydroxyphenyl)thiazol-2-yl)isobutyramide | 38.2 | 0.4 µg/mL |
| Potassium sorbate | 42.0 | 200 µg/mL |
| N-(4-(2,4-Dihydroxyphenyl)thiazol-2-yl)isobutyramide + potassium sorbate | 62.7 | 200.4 µg/mL |

Synthesis Procedures of Alkylamidothiazoles Selected by Way of Example

2-Bromo-2',4'-bismethoxycarbonyloxyacetophenone

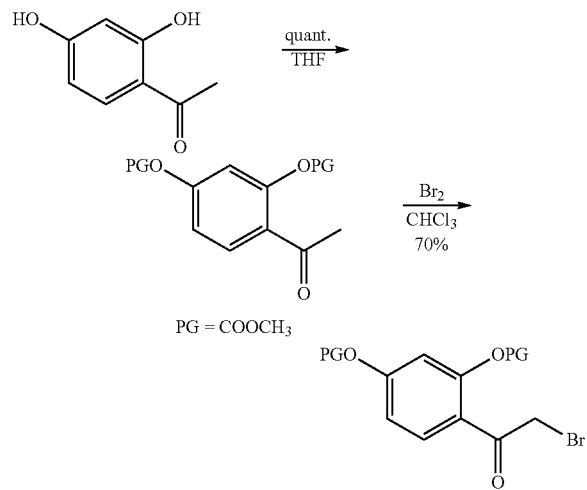

PG = COOCH₃

Mitchell, David; Doecke, Christopher W.; Hay, Lynne A.; Koenig, Thomas M.; Wirth, David D. Tetrahedron Letters, 1995

A solution of 60 g (369 mmol) of 2,4-dihydroxyacetophenone and 186 ml of triethylamine in 900 ml of tetrahydrofuran was cooled to 0° C., and 93 ml of methyl chloroformate in 400 ml of tetrahydrofuran was slowly added dropwise. A white precipitate is formed. After stirring for 3 hours at room temperature, the reaction is complete (TLC control). The precipitate was filtered off with suction and washed with copious amounts of tetrahydrofuran. The filtrate was evaporated to dryness on a rotary evaporator, taken up in ethyl acetate, washed with 1N HCl and NaCl solution (sat.) and dried over magnesium sulfate, filtered from the magnesium sulfate, and the ethyl acetate was concentrated on a rotary evaporator. This gave 105 g of 2,4-bismethoxycarbonyloxyacetophenone. $^1$H NMR (DMSO-D$_6$): 8.05 (d, 1H), 7.38 (d, 1H), 7.36 (s, 1H), 3.86 (d, 6H). The product was used without further purification. 63 g (392 mmol) of bromine in 450 ml of chloroform were added dropwise to the solution of 105 g of 2,4-bismethoxycarbonyloxyacetophenone in chloroform (1000 ml) over the course of 3 h. The reaction was then stirred for a further 15 min at room temperature. The solvent was evaporated on a rotary evaporator. The residue was stirred in ethyl acetate/n-hexane, and the resulting precipitate was filtered off with suction. Recrystallization from ethyl acetate/n-hexane produced 100 g of 2-bromo-2',4'-bismethoxycarbonyloxyacetophenone. $^1$H NMR (DMSO-D$_6$): 8.11 (d, 1H), 7.42 (m, 2H), 4.87 (s, 2H), 3.87 (s, 3H), 3.85 (s, 3H) ppm; m.p. 73-74° C.

N-(4-(2,4-Dihydroxyphenyl)thiazol-2-yl)pivalamide

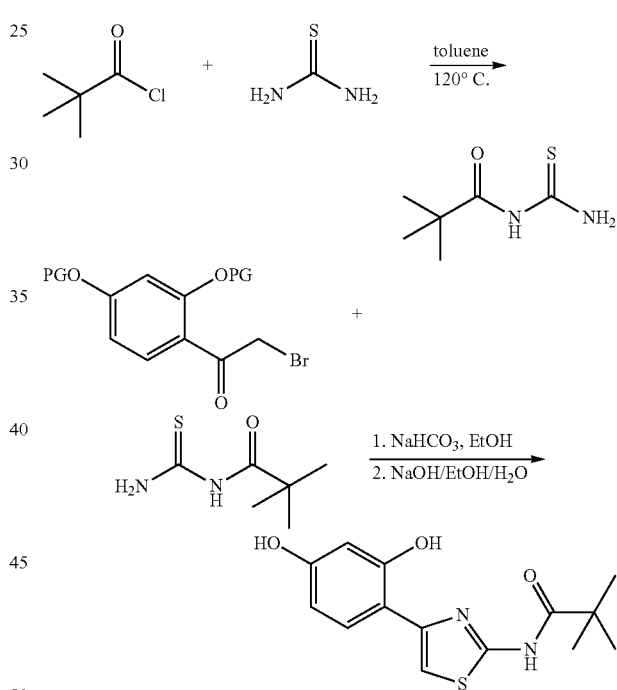

126 g (1.66 mmol) of thiourea were introduced into toluene (1000 ml), and 100 g (829 mmol) of pivaloyl chloride were added dropwise. The reaction solution was boiled under reflux for 3 hours, during which two phases formed. The upper phase was decanted off and cooled. The precipitated colorless needles were filtered off with suction and washed with cyclohexane and dried in vacuo. Yield: 64 g. $^1$H NMR (DMSO-D$_6$): 10.27 (s, 1H), 9.74 (s, 1H), 9.40 (s, 1H), 1.19 (s, 9H) ppm.

107.7 g (310 mmol) of 2-bromo-2',4'-bismethoxycarbonyloxyacetophenone were boiled with 49.7 g (13.6 mmol) of N-pivaloylthiourea and 39.2 g (466 mmol) of NaHCO₃ in 1.2 l of ethanol under reflux for 0.5 h. The reaction solution was cooled and admixed with 50.6 g (1.27 mol) of NaOH in 250 ml of water. After stirring for 30 min at room temperature, the reaction solution was taken up with 300 ml of water and neutralized with 2N HCl. The resulting precipitate was filtered off and recrystallized from ethanol/water. 80 g of thiazole were obtained. $^1$H NMR (DMSO-D$_6$): 11.77 (bs, 1H), 11.02 (bs, 1H), 9.47 (bs, 2H), 7.65 (d, 1H), 7.39 (s, 1H), 6.30 (s, 1H), 6.28 (d, 1H), 1.27 (s, 9H) ppm; m.p. 257-259° C.

N-(4-(2,4-Dihydroxyphenyl)thiazol-2-yl)isobutyramide

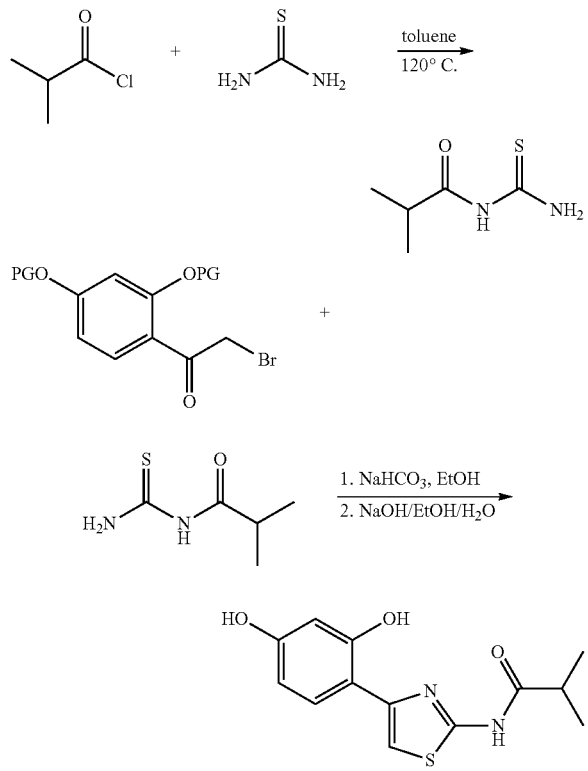

114 g (1.5 mol) of thiourea were introduced into toluene (800 ml), and 80 g (0.75 mol) of iso-butyryl chloride were added dropwise. The reaction solution was boiled under reflux for 3 hours, during which two phases formed. The upper phase was decanted off and cooled. The precipitated white crystals were filtered off with suction and washed with toluene and dried in vacuo. Yield: 62 g. $^1$H NMR (DMSO-D$_6$): 11.03 (bs, 1H), 9.66 (bs, 1H), 9.35 (bs, 1H), 2.72 (m, 1H), 1.03 (d, 6H) ppm.

89 g (260 mmol) of 2-bromo-2',4'-bismethoxycarbonyloxyacetophenone were boiled under reflux with 37.5 g (260 mmol) of N-isobutyrylthiourea and 32 g (380 mmol) of NaHCO$_3$ in 1000 ml of ethanol for 0.5 h. The reaction solution was cooled and admixed with 41 g (0.93 mol) of NaOH in 250 ml of water. After stirring for 30 min at room temperature, the reaction solution was taken up with 300 ml of water and adjusted to pH=3 with 2N HCl. The resulting precipitate was filtered off and recrystallized from ethanol/water. 56 g of thiazole were obtained. $^1$H NMR (DMSO-D$_6$): 12.16 (bs, 1H), 10.88 (bs, 1H), 9.47 (bs, 1H), 7.65 (m, 1H), 7.41 (s, 1H), 6.32 (m, 2H), 2.75 (m, 1H), 1.14 (d, 6H) ppm; m.p. 243-245° C.

N-(4-(2,4-Dihydroxyphenyl)thiazol-2-yl)butyramide

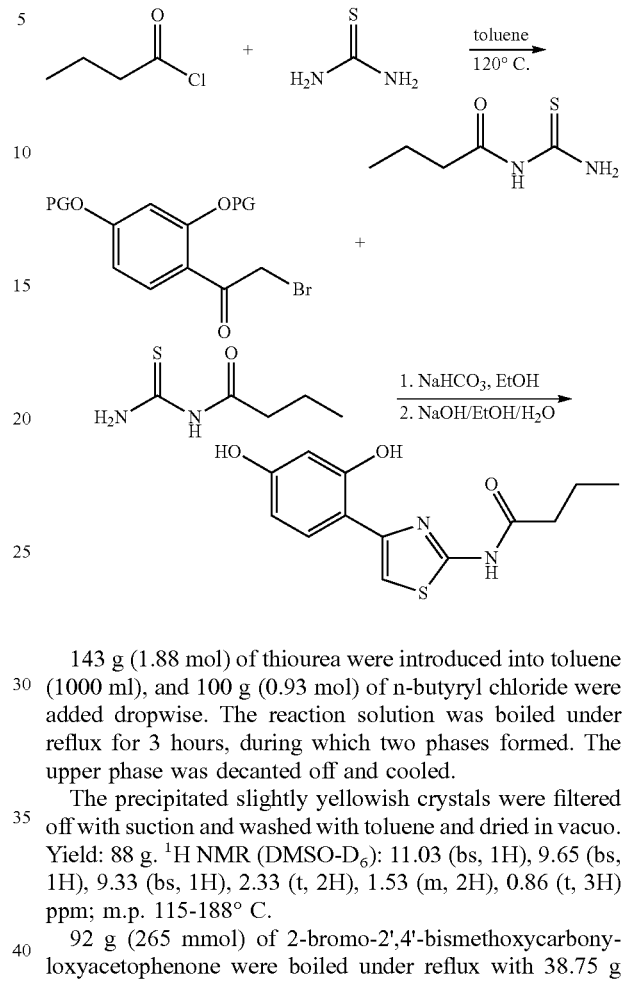

143 g (1.88 mol) of thiourea were introduced into toluene (1000 ml), and 100 g (0.93 mol) of n-butyryl chloride were added dropwise. The reaction solution was boiled under reflux for 3 hours, during which two phases formed. The upper phase was decanted off and cooled.

The precipitated slightly yellowish crystals were filtered off with suction and washed with toluene and dried in vacuo. Yield: 88 g. $^1$H NMR (DMSO-D$_6$): 11.03 (bs, 1H), 9.65 (bs, 1H), 9.33 (bs, 1H), 2.33 (t, 2H), 1.53 (m, 2H), 0.86 (t, 3H) ppm; m.p. 115-188° C.

92 g (265 mmol) of 2-bromo-2',4'-bismethoxycarbonyloxyacetophenone were boiled under reflux with 38.75 g (265 mmol) of N-butyrylthiourea and 34 g (397 mmol) of NaHCO$_3$ in 900 ml of ethanol for 0.5 h. The reaction solution was cooled and admixed with 37 g (0.93 mol) of NaOH in 300 ml of water. After stirring for 30 min at room temperature, the reaction solution was taken up with 300 ml of water and neutralized with 2N HCl. The resulting precipitate was filtered off and recrystallized from ethanol/water. 67 g of thiazole were obtained. $^1$H NMR (DMSO-D$_6$): 12.18 (bs, 1H), 10.89 (bs, 1H), 9.48 (bs, 1H), 7.65 (1 arom. H), 7.40 (s, 1H), 6.31 (2 arom. H), 2.43 (t, 2H), 1.64 (m, 2H), 0.91 (t, 3H) ppm; m.p. 227-229° C.

N-(4-(2,4-Dihydroxyphenyl)thiazol-2-yl)acetamide

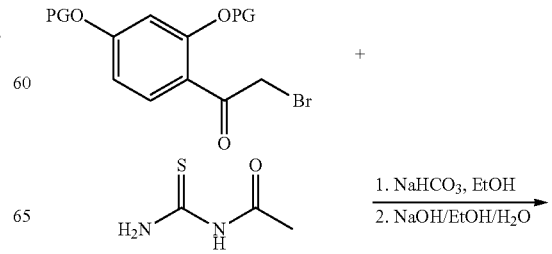

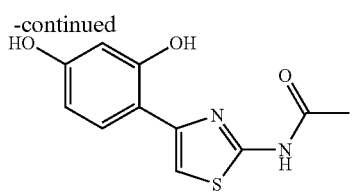

4.71 g (13.6 mmol) of 2-bromo-2',4'-bismethoxycarbonyloxyacetophenone were boiled under reflux with 1.61 g (13.6 mmol) of N-acetylthiourea and 1.72 g (20.4 mmol) of NaHCO₃ in 45 ml of ethanol for 0.5 h. The reaction solution was cooled and admixed with 2.0 g (50 mmol) of NaOH in 20 ml of water. After stirring for 20 min at 0° C., the reaction solution was taken up with 30 ml of water and neutralized with semi-concentrated HCl. The resulting precipitate was filtered off and recrystallized from ethanol/water. 2.73 g of product were obtained. ¹H NMR (DMSO-D₆): 12.20 (b, 1H), 10.85 (s, 1H), 9.46 (s, 1H), 7.64 (m, 1H), 7.38 (s, 1H), 6.28 (m, 2H), 2.15 (s, 3H) ppm; m.p. 264-264° C.

N-(4-(2,4-Dihydroxyphenyl)thiazol-2-yl)-4-(hydroxymethyl)cyclohexanecarboxamide

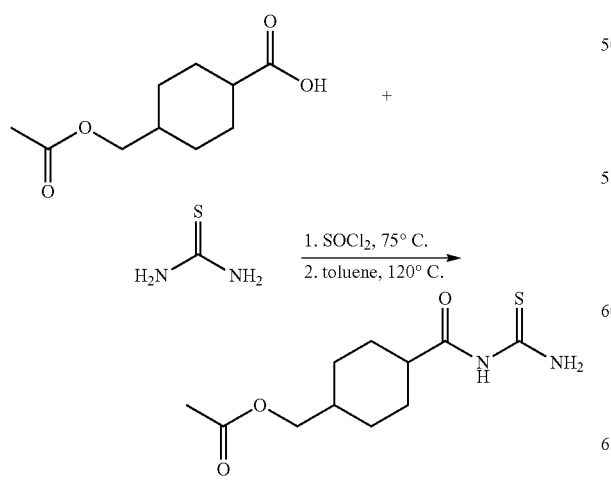

Procedure Analogous to the Literature.
BANYU Pharmaceutical Co. Ltd., EP2072519 A1, 2009
Yield: 96%. ¹H NMR (DMSO-D₆): 12.03 (bs, 1H), 3.85, 3.82 (2×d, 2H), 2.50, 2.47 (2×m, 1H), 2.00 (s, 3H), 0.95-1.90 (m, 9H) ppm

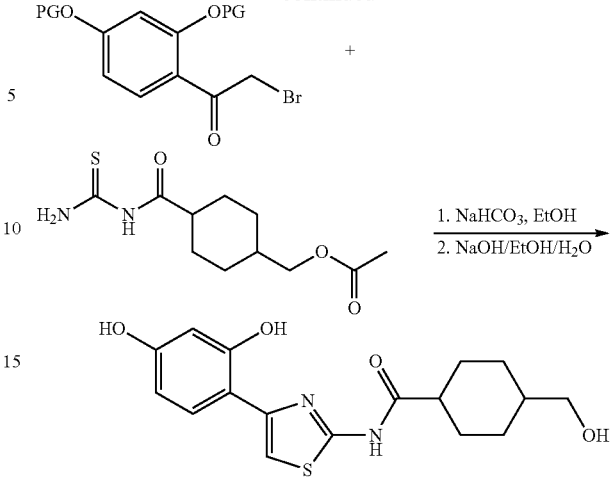

95 g (0.47 mol) of 4-acetoxymethylcyclohexanecarboxylic acid were heated under reflux in 350 ml of thionyl chloride for 2 h. After removing the excess thionyl chloride in vacuo, the residue was taken up in 1 l of toluene, and 71 g (0.94 mol) of thiourea were added. The reaction solution was boiled under reflux for 3 hours and then filtered off while hot. After cooling the mother liquor, the resulting white crystals were filtered off with suction, washed with toluene and dried in vacuo. Yield: 59 g. ¹H NMR (DMSO-D₆): 11.03, 10.97 (2×s, 1H), 9.64 (bs, 1H), 9.35 (bs, 1H), 3.93, 3.82 (2×d, 2H), 2.61, 2.42 (2×m, 1H), 2.00 (s, 3H), 1.60 (m, 8H), 1.35, 0.94 (2×m, 1H) ppm.

79 g (228 mmol) of 2-bromo-2',4'-bismethoxycarbonyloxyacetophenone were boiled under reflux for 0.5 h with 59 g (228 mmol) of N-(4-acetoxymethylcyclohexylcarbonyl)thiourea and 29 g (340 mmol) of NaHCO₃ in 1000 ml of ethanol. The reaction solution was cooled and admixed with 73 g (1.8 mol) of NaOH in 300 ml of water. After stirring for 30 min at room temperature, the reaction solution was taken up with 300 ml of water and adjusted to pH=3 with 2N HCl. The resulting precipitate was filtered off and recrystallized from ethanol/water. 47 g of thiazole were obtained. ¹H NMR (DMSO-D₆): 12.15, 12.10 (2×s, 1H), 10.96 (2×s, 1H), 9.47 (br, 2H), 7.64 (d, 1H), 7.39 (s, 1H), 6.29 (m, 2H), 4.40 (br, 1H), 3.32, 3.23 (2×d, 2H), 2.65, 2.44 (2×m, 1H), 1.90 (m, 1H), 1.78 (m, 2H), 1.50 (m, 5H), 0.94 (m, 1H) ppm; m.p. 152-160° C.

N-(4-(2,4-Dihydroxyphenyl)thiazol-2-yl)cyclohexanecarboxamide

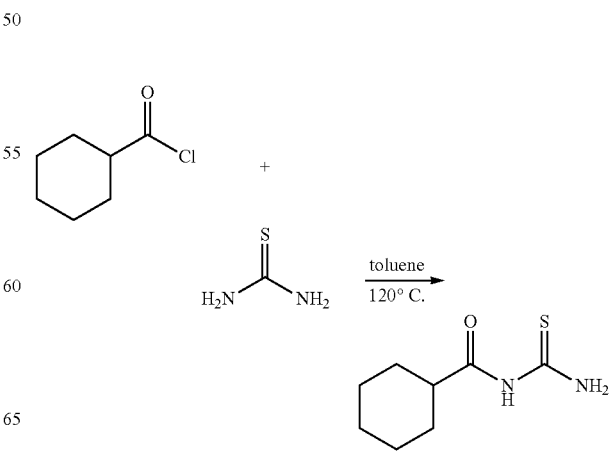

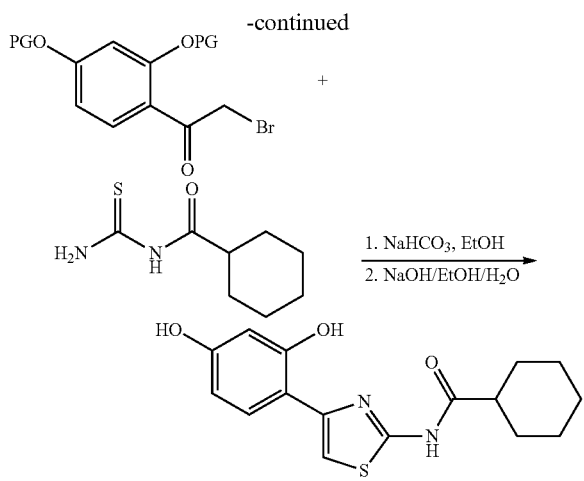

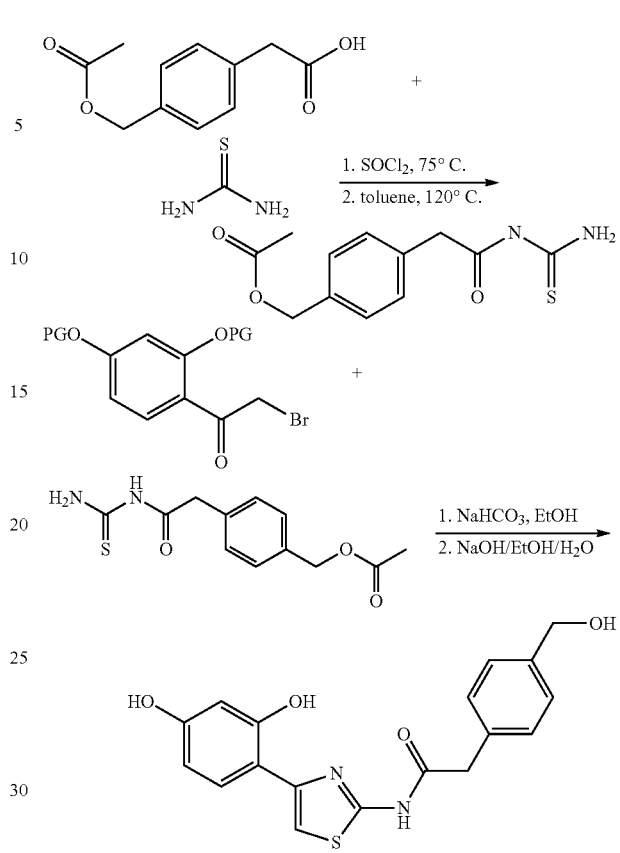

52 g (0.68 mol) of thiourea were introduced into toluene (500 ml), and 50 g (0.34 mol) of cyclohexanoyl chloride were added dropwise. The reaction solution was boiled under reflux for 3 hours, during which two phases formed. The upper phase was decanted off and cooled. The precipitated crystals were filtered off with suction, washed with toluene and recrystallized from methanol. Yield: 35 g. $^1$H NMR (DMSO-D$_6$): 10.98 (bs, 1H), 9.65 (bs, 1H), 9.32 (bs, 1H), 2.49 (t, 1H), 1.75 (m, 4H), 1.61 (m, 1H), 1.18 (m, 5H) ppm.

92 g (265 mmol) of 2-bromo-2',4'-bismethoxycarbonyloxyacetophenone were boiled under reflux for 0.5 h with 49.4 g (265 mmol) of N-cyclohexanoylthiourea and 34 g (397 mmol) of NaHCO$_3$ in 900 ml of ethanol. The reaction solution was cooled and admixed with 37 g (930 mmol) of NaOH in 300 ml of water. After stirring for 30 min at room temperature, the reaction solution was taken up with 300 ml of water and neutralized with 2N HCl. The ethanol was largely removed on a rotary evaporator. The precipitate formed was filtered off and recrystallized from ethanol/water. 70 g of thiazole were obtained. $^1$H NMR (DMSO-D$_6$): 12.14 (bs, 1H), 11.00 (bs, 1H), 9.48 (bs, 1H), 7.64 (1 arom. H), 7.39 (s, 1H), 6.30 (2 arom. H), 2.49 (m, 1H), 1.84 (m, 2H), 1.76 (m, 2H), 1.65 (m, 1H), 1.42 (m, 2H), 1.25 (m, 3H), ppm; m.p.: 262-266° C.

N-(4-(2,4-Dihydroxyphenyl)thiazol-2-yl)-2-(4-(hydroxymethyl)phenyl)acetamide

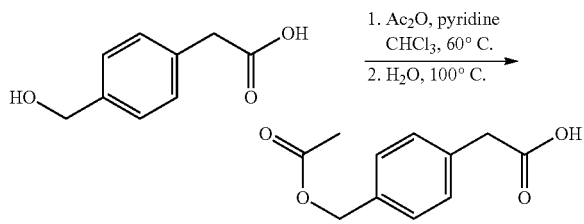

Procedure Analogous to the Literature.
BANYU Pharmaceutical Co. Ltd., EP2072519 A1, 2009
Yield: 76%. $^1$H NMR (DMSO-D$_6$): 12.31 (bs, 1H), 7.26 (m, 4H), 5.05 (s, 2H), 3.57 (s, 2H), 2.05 (s, 3H) ppm 3.7 g (18 mmol) of 4-acetoxymethylphenylacetic acid were heated under reflux in 40 ml of thionyl chloride for 2 h. After removing the excess thionyl chloride in vacuo, the residue was taken up in 70 ml of toluene, and 2.7 g (36 mmol) of thiourea were added. The reaction solution was boiled under reflux for 3 hours and then the solvent was removed in vacuo. Purification was by means of column chromatography with cyclohexane/ethyl acetate 1/1 on silica gel. Yield: 2.7 g. $^1$H NMR (DMSO-D$_6$): 11.29 (bs, 1H), 9.55 (bs, 1H), 9.40 (bs, 1H), 7.30 (m, 4H), 5.04 (s, 2H), 3.71 (s, 2H), 2.05 (s, 3H) ppm.

3.5 g (10 mmol) of 2-bromo-2',4'-bismethoxycarbonyloxyacetophenone were boiled under reflux for 0.5 h with 2.7 g (10 mmol) of N-[2-(4-acetoxymethylphenyl)acetyl]thiourea and 1.3 g (15 mmol) of NaHCO$_3$ in 50 ml of ethanol. The reaction solution was cooled and admixed with 4.0 g (0.1 mol) of NaOH in 20 ml of water. After stirring for 2 h at 60° C., the reaction solution was taken up in 100 ml of water and adjusted to pH=3 with 2N HCl. The resulting precipitate was filtered off and recrystallized from ethanol/water. 1.3 g of thiazole were obtained.

$^1$H NMR (DMSO-D$_6$): 12.44 (s, 1H), 10.80 (s, 1H), 9.48 (s, 1H), 7.66 (d, 1H), 7.41 (s, 1H), 7.29 (m, 4H), 6.32 (m, 2H), 5.13 (t, 1H), 4.47 (d, 2H), 3.77 (s, 2H) ppm; m.p. 254-256° C.

Cosmetic or dermatological preparations with a content of alkylamidothiazoles and their use for the treatment and/or prophylaxis of undesired skin pigmentation are likewise advantageous embodiments of the present invention.

It is particularly advantageous if such preparations comprise 0.000001 to 10% by weight, in particular 0.0001 to 3% by weight, very particularly 0.001 to 1% by weight, of one or more of the alkylamidothiazoles used according to the invention, based on the total weight of the preparation.

Cosmetic and dermatological preparations according to the invention can be in various forms. Thus, they can be e.g. a solution, an anhydrous preparation, an emulsion or microemulsion of the water-in-oil (W/O) type or of the oil-in-water (O/W) type, a multiple emulsions, for example of the water-in-oil-in-water (W/O/W) type, a gel, a solid stick, a balm or else an aerosol. It is also advantageous according to the invention to administer the substances used according to the invention and/or their derivatives in encapsulated form, e.g. in collagen matrices and other customary encapsulation materials, e.g. as cellulose encapsulations, in gelatin or liposomally encapsulated.

It is also possible and advantageous in the context of the present invention to add the substances used according to the invention and/or their derivatives in aqueous systems or surfactant preparations for cleaning the skin and the hair.

The cosmetic and dermatological preparations according to the invention can comprise cosmetic auxiliaries as are customarily used in such preparations, e.g. preservatives, bactericides, perfumes, substances for preventing foaming, dyes, pigments which have a coloring effect, thickeners, surface-active substances, emulsifiers, softening, moisturizing and/or humectant substances, fats, oils, waxes or other customary constituents of a cosmetic or dermatological formulation such as alcohols, polyols, polymers, foam stabilizers, electrolytes, organic solvents or silicone derivatives.

The lipid phase can advantageously be selected from the following substance group:

mineral oils, mineral waxes oils, such as triglycerides of capric acid or of caprylic acid, also natural oils such as e.g. castor oil;

fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;

alkyl benzoates;

silicone oils such as dimethylpolysiloxanes, diethylpolysiloxanes, diphenylpolysiloxanes and mixtures thereof.

The oil phase of the emulsions, oleogels or hydrodispersions or lipodispersions within the context of the present invention is advantageously selected from the group of esters of saturated and/or unsaturated, branched and/or unbranched alkanecarboxylic acids of chain length from 3 to 30 C atoms and saturated and/or unsaturated, branched and/or unbranched alcohols of chain length from 3 to 30 C atoms, from the group of esters of aromatic carboxylic acids and saturated and/or unsaturated, branched and/or unbranched alcohols of chain length from 3 to 30 C atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

The aqueous phase of the preparations according to the invention optionally advantageously comprises humectants such as e.g. propylene glycol, panthenol or hyaluronic acid, and in particular one or more thickeners which can advantageously be selected from the group silicon dioxide, aluminum silicates, hydroxypropylmethylcellulose, particularly advantageously a polyacrylate such as, for example, carbopol grade 980, in each case individually or in combination.

In particular, mixtures of the aforementioned solvents are used. In the case of alcoholic solvents, water can be a further constituent.

Emulsions according to the invention are advantageous and comprise e.g. the specified fats, oils, waxes and other fatty bodies, as well as water and an emulsifier, as is customarily used for such a type of formulation.

Gels according to the invention usually comprise alcohols of low carbon number, e.g. ethanol, propylene glycol, and water or an aforementioned oil in the presence of a thickener which, in the case of oily-alcoholic gels, is preferably silicon dioxide or an aluminum silicate, and in the case of aqueous-alcoholic or alcoholic gels is preferably a polyacrylate.

Suitable propellants for preparations according to the invention that can be sprayed from aerosol containers are the customary known readily volatile, liquefied propellants, for example hydrocarbons (propane, butane, isobutane), which can be used on their own or in a mixture with one another. Compressed air is also to be used advantageously.

Advantageously, preparations according to the invention can furthermore advantageously comprise substances which absorb UV radiation in the UVB region, the total amount of the filter substances being e.g. 0.1% by weight to 30% by weight, preferably 0.5 to 10% by weight, in particular 1.0 to 6.0% by weight, based on the total weight of the preparations, in order to provide cosmetic preparations which protect the hair and/or the skin from the entire range of ultraviolet radiation. They can also serve as sunscreens for the hair or the skin.

Furthermore, preparations according to the invention can advantageously additionally comprise substances which conceal the troublesome intrinsic odor of the remaining raw materials used, the total amount of the perfume ingredients being e.g. 0.001% by weight to 30% by weight, preferably 0.05 to 10% by weight, in particular 0.1 to 5.0% by weight, based on the total weight of the preparations, in order to provide cosmetic preparations.

DETAILED DESCRIPTION OF THE INVENTION

The examples below are intended to illustrate the present invention without limiting it. Unless stated otherwise, all of the quantities, fractions and percentages stated are based on the weight and the total amount or on the total weight of the preparations.

FORMULATION EXAMPLES

O/W Emulsions

| | Formulation example | | | |
|---|---|---|---|---|
| | 1 | 2 | 3 | 4 |
| Chemical/INCI name | % by wt. | % by wt. | % by wt. | % by wt. |
| Stearic acid | 2.50 | 2.00 | 2.00 | 2.50 |
| Glyceryl stearate | 1.00 | 1.00 | 1.00 | 1.00 |
| C12-15 alkyl benzoate | 3.00 | 5.00 | 3.00 | 2.00 |
| Caprylic/capric triglyceride | 2.50 | 2.50 | 2.00 | 2.50 |
| Isopropyl palmitate | 2.00 | — | — | 2.00 |
| Cetylstearyl alcohol | 3.00 | — | 2.00 | 3.00 |

| Chemical name | | | | |
|---|---|---|---|---|
| Cetyl alcohol | — | 2.00 | — | — |
| Stearyl alcohol | — | 2.00 | 1.00 | — |
| C13-16 Isoparaffin | — | — | — | 1.00 |
| Dibutyl adipate | — | — | 1.50 | — |
| Cyclomethicone | 1.00 | 1.00 | 0.50 | — |
| Dicaprylyl carbonate | 2.00 | 2.00 | 2.00 | 2.00 |
| Dimethicone | 1.00 | — | 0.50 | 1.00 |
| Glycerol | 5.00 | 7.00 | 5.00 | 9.00 |
| Ethylhexyl cocoate | — | — | 1.00 | — |
| Methylparaben | 0.20 | — | — | — |
| Phenoxyethanol | 0.40 | 0.50 | 0.50 | 0.40 |
| Propylparaben | 0.10 | — | — | 0.10 |
| 1,2-Hexanediol | — | — | 0.10 | 0.10 |
| Ethylhexylglycerol | — | — | 0.20 | — |
| Methylisothiazolinone | — | 0.05 | — | — |
| Butylene glycol | — | — | 2.0 | — |
| Carbomer | 0.15 | 0.10 | 0.15 | 0.10 |
| Carrageenan | 0.10 | — | 0.10 | — |
| Xanthan Gum | — | — | 0.10 | — |
| Acrylates/C10-30 Alkyl Acrylate Crosspolymer | — | 0.10 | — | 0.10 |
| Trisodium EDTA | 0.20 | 0.20 | 0.20 | 0.20 |
| Tapioca starch | 1.50 | 1.00 | — | — |
| Nylon-12 (1,8-diazacyclo-tetradecane-2,7-dione homopolymer) | — | 0.20 | — | 0.50 |
| Polymethylsilsesquioxane | — | 1.00 | 1.00 | — |
| Aluminum starch octenylsuccinate | — | — | 1.00 | — |
| Distarch phosphate | 1.00 | 1.00 | — | 1.00 |
| Butylmethoxydibenzoylmethane | 1.00 | 2.00 | 1.00 | 1.00 |
| Phenylbenzimidazolesulfonic acid | 1.00 | 1.00 | 2.00 | 2.00 |
| Octocrylene | 2.00 | 2.00 | 1.00 | 2.00 |
| Ethylhexyl salicylate | 1.00 | 1.00 | 2.00 | 1.00 |
| Sodium benzoate | 0.01 | 0.05 | 0.10 | 0.15 |
| Dehydroacetic acid | 0.10 | 0.05 | 0.20 | 0.03 |
| Hydroxypropyltetrahydropyranetriol | 1.00 | 0.50 | — | — |
| Lipoic acid | — | 0.50 | 0.20 | — |
| Potassium methoxysalicylate | 0.30 | — | 0.10 | 0.05 |
| Vitamin B6 HCl | 0.10 | 0.05 | — | 0.30 |
| Tranexamic acid | — | 0.01 | 0.25 | — |
| *Pyrus Malus* Stem Extract | 1.00 | 0.25 | 0.50 | 0.75 |
| N-(4-(2,4-Dihydroxyphenyl)thiazol-2-yl)isobutyramide | 0.20 | 0.10 | 0.05 | 0.30 |
| N-(4-(2,4-Dihydroxyphenyl)thiazol-2-yl)pivalamide | 0.01 | 0.25 | 0.15 | 0.10 |
| N-(4-(2,4-Dihydroxyphenyl)thiazol-2-yl)butyramide | 0.25 | 0.15 | 0.30 | 0.35 |
| N-(4-(2,4-Dihydroxyphenyl)thiazol-2-yl)cyclohexancarboxamide | 0.10 | 0.10 | 0.15 | 0.20 |
| Sodium hydroxide | q.s. | q.s. | q.s. | q.s. |
| Hydroxyisohexyl 3-cyclohexenecarboxaldehyde | 0.10 | — | — | 0.05 |
| Citronellol | 0.05 | 0.10 | — | 0.05 |
| Linalool | — | 0.05 | 0.10 | — |
| Perfume | 0.30 | 0.20 | 0.20 | 0.20 |
| Sodium hydroxide | q.s. | q.s. | q.s. | q.s. |
| Water | ad 100 | ad 100 | ad 100 | ad 100 |

Formulation example

| Chemical name | 5 % by wt. | 6 % by wt. | 7 % by wt. | 8 % by wt. |
|---|---|---|---|---|
| Glyceryl stearate citrate | 2.00 | 1.50 | 2.00 | 2.00 |
| Behenyl alcohol | 1.50 | 1.00 | 1.00 | 1.00 |
| C12-15 Alkyl benzoate | 2.00 | 2.50 | 2.00 | 2.50 |
| Caprylic/capric triglyceride | 2.00 | 2.50 | 2.50 | 2.50 |
| Cetyl alcohol | 2.00 | 2.00 | — | 2.00 |
| Cetylstearyl alcohol | — | — | 2.00 | — |
| Cyclopentasiloxane | — | — | — | 1.00 |
| Cyclomethicone | 1.00 | 1.00 | 2.00 | 2.00 |
| Dicaprylyl carbonate | — | 2.00 | 2.50 | 2.50 |
| Paraffinum Liquidum (mineral oil) | — | — | 0.50 | — |
| Octyldodecanol | — | 2.00 | — | — |
| Isopropyl palmitate | 1.50 | — | — | — |
| Dimethicone | 0.50 | 1.00 | 1.00 | — |
| Glycerol | 3.00 | 5.00 | 7.00 | 9.00 |
| Methylparaben | 0.20 | 0.15 | — | — |
| Phenoxyethanol | 0.40 | 0.60 | 0.50 | 0.50 |
| Propylparaben | 0.10 | — | — | — |
| Methylisothiazolinone | — | — | 0.05 | — |
| Piroctone olamine | — | — | — | 0.15 |
| Sodium benzoate | 0.10 | 0.10 | 0.10 | 0.10 |
| Glyceryl caprylate | — | — | — | 0.20 |
| Ethylparaben | 0.10 | — | — | — |
| Carbomer | 0.20 | — | 0.15 | 0.15 |
| Sodium polyacrylate | — | 0.40 | — | — |
| Xanthan gum | 0.10 | — | 0.10 | — |
| Acrylates/C10-30 Alkyl Acrylate Crosspolymer | — | 0.10 | — | 0.10 |
| Tapioca starch | 0.50 | — | 0.50 | — |
| Nylon-12 (1,8-Diazacyclo-tetradecane-2,7-dione homopolymer) | 1.00 | — | — | 1.00 |
| Polymethylsilsesquioxane | — | 1.00 | 1.00 | — |
| Aluminum starch octenylsuccinate | — | 1.00 | — | 1.00 |
| N-(4-(2,4-Dihydroxyphenyl)thiazol-2-yl)isobutyramide | 0.25 | 0.15 | 0.30 | 0.35 |
| N-(4-(2,4-Dihydroxyphenyl)thiazol-2-yl)pivalamide | 0.10 | 0.10 | 0.15 | 0.20 |
| N-(4-(2,4-Dihydroxyphenyl)thiazol-2-yl)butyramide | 0.01 | 0.25 | 0.15 | 0.10 |
| N-(4-(2,4-Dihydroxyphenyl)thiazol-2-yl)cyclohexanecarboxamide | 0.20 | 0.10 | 0.05 | 0.30 |
| *Glycyrrhiza Inflata* Root Extract | 0.03 | 0.05 | 0.05 | 0.03 |
| Titanium dioxide | — | 1.00 | — | — |
| Octocrylene | 1.00 | 2.00 | 1.00 | 1.00 |
| Bis-Ethylhexyloxyphenol Methoxyphenyl Triazine | 1.00 | 1.00 | 2.00 | 2.00 |
| 2-Ethylhexylmethoxycinnamate | 2.00 | 2.00 | 1.00 | 2.00 |
| Homosalate (3,3,5-Trimethyl-cyclohexyl salicylate) | 1.00 | 1.00 | 2.00 | 1.00 |
| Sodium hydroxide | q.s. | q.s. | q.s. | q.s. |
| Trisodium EDTA | 0.15 | — | 0.15 | — |
| 1-(1,2,3,4,5,6,7,8-octahydro-2,3,8,8,-tetramethyl-2-naphthyl)ethan-1-one | 0.1 | — | q.s. | q.s. |
| Geraniol | — | 0.05 | — | — |
| Hexylcinnamal | — | — | 0.05 | — |
| Perfume | 0.10 | 0.20 | 0.30 | 0.20 |
| Water | ad 100 | ad 100 | ad 100 | ad 100 |

Formulation examples

| Chemical name | 9 % by wt. | 10 % by wt. | 11 % by wt. | 12 % by wt. |
|---|---|---|---|---|
| Polyglyceryl-3 Methylglucose Distearate | 2.00 | 2.50 | 2.50 | 2.50 |
| Sorbitan Stearate | 1.50 | 3.00 | 1.50 | 3.00 |
| C12-15 Alkyl benzoate | 2.50 | 2.50 | 2.50 | 2.50 |
| Caprylic/capric triglycerides | 2.50 | 2.50 | 2.50 | 2.50 |
| Stearyl alcohol | 1.00 | 1.50 | 1.00 | 1.50 |
| Cyclomethicone | 3.00 | 1.00 | 2.00 | 1.00 |
| Isopropyl myristate | — | 2.50 | 2.00 | 2.50 |
| Isopropyl palmitate | 2.00 | — | 1.00 | — |
| Ethylhexyl stearate | — | 1.50 | — | — |
| Dimethicone | — | 1.00 | — | 1.00 |
| Decyl Oleate | — | — | 1.50 | — |
| Glycerol | 5.00 | 7.50 | 3.00 | 7.50 |
| *Butyrospermum Parkii* Butter | 2.00 | — | — | — |
| Squalane | 0.50 | — | — | — |
| Sodium benzoate | 0.10 | 0.10 | 0.10 | 0.10 |
| Methylparaben | 0.20 | 0.20 | — | 0.10 |

-continued

| Chemical name | | | | |
|---|---|---|---|---|
| Phenoxyethanol | 0.40 | 0.40 | 0.40 | 0.40 |
| Propylparaben | 0.10 | — | — | — |
| Benzethonium chloride | — | — | 0.10 | — |
| Caprylyl glycol | — | 0.20 | — | — |
| Ethylhexylglycerol | — | 0.20 | — | 0.2 |
| Pentylene glycol | — | 0.10 | 0.05 | 0.5 |
| Carbomer | 0.15 | 0.10 | 0.15 | 0.10 |
| Ammonium Acryloyldimethyl-taurate/VP Copolymer | — | 0.20 | — | 0.20 |
| Carrageenan | 0.10 | — | 0.15 | — |
| Trisodium EDTA | — | 1.00 | — | 1.00 |
| Tapioca starch | — | 1.00 | 1.00 | — |
| Distarch phosphate | — | 1.00 | — | 1.00 |
| Acrylonitrile-methacrylonitrile-methyl-methacrylate Copolymer + Isopentane + Magnesium Hydroxide | — | — | 1.00 | 1.00 |
| N-(4-(2,4-Dihydroxy-phenyl)thiazol-2-yl)isobutyramide | 0.01 | 0.25 | 0.15 | 0.10 |
| N-(4-(2,4-Dihydroxy-phenyl)thiazol-2-yl)pivalamide | 0.20 | 0.10 | 0.05 | 0.30 |
| N-(4-(2,4-Dihydroxy-phenyl)thiazol-2-yl)butyramide | 0.25 | 0.15 | 0.30 | 0.35 |
| N-(4-(2,4-Dihydroxy-phenyl)thiazol-2-yl)cyclohexanecarboxamide | 0.10 | 0.10 | 0.15 | 0.20 |
| Diethylamino Hydroxybenzoyl Hexyl Benzoate | 1.00 | 2.00 | 1.00 | 1.00 |
| Ethylhexyl methoxycinnamate | 1.00 | 1.00 | 2.00 | 2.00 |
| Butylmethoxydibenzoylmethane | 2.00 | 2.00 | 1.00 | 2.00 |
| Octocrylene | 1.00 | 1.00 | 2.00 | 1.00 |
| Titanium dioxide | — | — | 1.00 | — |
| Sodium hydroxide | q.s. | q.s. | q.s. | q.s. |
| Ubiquinone | 0.10 | — | — | — |
| Sodium metabisulfite | — | 0.15 | — | — |
| BHT (tert-butylhydroxytoluene) | — | — | 0.05 | — |
| Linalyl acetate | 0.05 | — | — | — |
| Hexyl salicylate | — | 0.05 | — | — |
| Benzyl salicylate | — | — | 0.01 | — |
| Perfume | q.s. | q.s. | q.s. | q.s. |
| Water | ad 100 | ad 100 | ad 100 | ad 100 |

| | Formulation examples | | | |
|---|---|---|---|---|
| Chemical name | 13 % by wt. | 14 % by wt. | 15 % by wt. | 16 % by wt. |
| PEG-40 Stearate | 0.80 | 1.00 | 1.00 | 1.00 |
| Glyceryl Stearate | 2.50 | 3.00 | 3.00 | 3.00 |
| C12-15 Alkyl Benzoate | 2.00 | 2.50 | 2.00 | 2.00 |
| Caprylic/capric triglyceride | 2.00 | 2.50 | 2.50 | 2.00 |
| Cetylstearyl alcohol | 3.00 | 3.00 | 3.00 | 3.00 |
| Cyclomethicone | 2.00 | 2.00 | 2.00 | 2.00 |
| Dicaprylyl carbonate | — | 2.00 | 2.50 | 2.50 |
| Octyldodecanol | 1.00 | — | — | 1.50 |
| Triisostearin | — | 0.50 | — | 1.00 |
| *Butyrospermum Parkii* Butter | 2.00 | — | — | — |
| Octyldodecyl myristate | 1.00 | — | 1.50 | — |
| Dimethicone | 1.00 | 1.00 | 1.00 | 1.00 |
| Glycerol | 7.50 | 5.00 | 9.0 | 7.50 |
| Methylparaben | 0.20 | — | 0.10 | — |
| Phenoxyethanol | 0.40 | 0.50 | 0.40 | 0.40 |
| Propylparaben | 0.10 | — | — | — |
| Glyceryl caprylate | — | 0.25 | — | — |
| Pentylene glycol | — | 0.50 | — | — |
| Butylene glycol | — | — | 3.00 | — |
| Lauroyl ethyl arginate | 0.10 | 0.05 | 0.20 | — |
| Potassium sorbate | 0.10 | 0.05 | 0.15 | 0.01 |
| Sodium salicylate | 0.01 | 0.02 | 0.01 | 0.05 |
| Carbomer | 0.15 | 0.10 | 0.10 | 0.15 |
| Sodium polyacrylate | — | 0.20 | 0.20 | — |
| Xanthan gum | 0.10 | — | — | — |

-continued

| Chemical name | | | | |
|---|---|---|---|---|
| Acrylates/C10-30 Alkyl Acrylate Crosspolymer | — | — | — | 0.1 |
| Trisodium EDTA + water (20% strength aqueous solution) | — | 1.00 | 1.00 | 1.00 |
| Tapioca starch | — | 1.00 | 1.00 | 1.00 |
| Distarch phosphate | — | 1.00 | 1.00 | 1.00 |
| Aluminum starch octenylsuccinate | 2.00 | — | — | — |
| Acrylonitrile-methacrylonitrile-methyl-methacrylate Copolymer + Isopentane + Magnesium Hydroxide | 1.00 | — | — | — |
| N-(4-(2,4-Dihydroxy-phenyl)thiazol-2-yl)-isobutyramide | 0.10 | 0.15 | 0.10 | 0.01 |
| Ethylhexyl methoxycinnamate | 1.00 | 2.00 | 1.00 | 1.00 |
| Diethylamino Hydroxybenzoyl Hexyl Benzoate | 0.50 | 1.00 | 2.00 | 1.00 |
| Homosalate (3,3,5-Trimethyl-cyclohexyl salicylate) | 2.00 | 2.00 | 1.00 | 2.00 |
| Phenylbenzimidazolesulfonic acid | 1.00 | 1.00 | 2.00 | 1.00 |
| Titanium dioxide | — | — | 1.00 | — |
| Glyceryl Glucoside | 3.00 | — | — | — |
| Short-chain hyaluronic acid | — | 0.10 | — | — |
| Long-chain hyaluronic acid | — | — | 0.10 | — |
| 4-Butylresorcinol | — | — | — | 0.30 |
| Magnolia bark extract | 0.10 | — | — | — |
| Octadecenedioic acid | — | 0.05 | — | — |
| Folic acid | — | — | 0.01 | — |
| Carnitine | — | — | — | 0.50 |
| Creatine | 0.10 | — | — | — |
| Alpha-Glucosylrutin | — | 0.01 | — | — |
| Taurine | — | — | 0.10 | — |
| Mulberry root extract | — | — | — | 0.20 |
| Sodium metabisulfite | 0.10 | — | — | — |
| Diethylhexyl syringylidenemalonate | 0.13 | 0.13 | | |
| Sodium hydroxide | q.s. | q.s. | q.s. | q.s. |
| 3-Methyl-5-phenyl-1-pentanol | 0.10 | — | — | — |
| Coumarin | — | 0.05 | — | — |
| Ethyllinalool | — | — | 0.10 | — |
| Ascorbyl palmitate | 0.10 | — | — | — |
| Perfume | q.s. | q.s. | q.s. | q.s. |
| Water | ad 100 | ad 100 | ad 100 | ad 100 |

| | Formulation examples | | | |
|---|---|---|---|---|
| Chemical name | 17 % by wt. | 18 % by wt. | 19 % by wt. | 20 % by wt. |
| Glyceryl Stearate Citrate | 2.00 | 2.00 | 2.00 | 2.00 |
| Isopropyl Palmitate | 3.00 | 2.00 | 3.00 | 1.00 |
| Cetylstearyl alcohol | 4.00 | 3.00 | 3.00 | — |
| Cetyl alcohol | — | — | — | 4.00 |
| Caprylic/capric triglyceride | 3.00 | 2.50 | 2.00 | 3.00 |
| C12-15 Alkyl benzoate | 3.00 | 2.50 | 2.00 | 2.00 |
| Cyclomethicone | 1.00 | — | 1.00 | — |
| Dicaprylyl carbonate | — | — | 2.50 | — |
| Dimethicone | — | 0.50 | — | — |
| Octyldodecyl myristate | — | 1.00 | — | — |
| Glycerol | 4.00 | 6.00 | 5.00 | 6.00 |
| Methylparaben | 0.20 | — | 0.10 | — |
| Phenoxyethanol | 0.40 | 0.40 | 0.40 | 0.40 |
| Piroctone olamine | — | — | — | 0.10 |
| Ethylhexylglycerol | — | 0.30 | — | — |
| Glyceryl Caprylate | — | 0.30 | — | — |
| 2-Methyl-1,3-propanediol | — | 2.00 | — | 2.00 |
| Sodium benzoate | 0.01 | — | 0.20 | 0.10 |
| Sodium salt of dehydroacetic acid | 0.01 | 0.05 | 0.10 | 0.02 |
| Carbomer | 0.20 | 0.10 | 0.15 | — |
| Sodium polyacrylate | — | 0.40 | — | — |
| Xanthan gum | 0.10 | — | — | 0.15 |
| Acrylates/C10-30 Alkyl Acrylate Crosspolymer | — | — | 0.10 | 0.20 |
| Acrylonitrile-methacrylonitrile-methyl-methacrylate Copolymer + Isopentane + Magnesium Hydroxide | 0.50 | — | 0.50 | — |

-continued

| Chemical name | | | | |
|---|---|---|---|---|
| Aluminum starch octenylsuccinate | — | 1.00 | — | 1.00 |
| Methyl Methacrylate Crosspolymer | 1.00 | — | — | 1.00 |
| *Glycyrrhiza Inflata* root extract | 0.03 | — | — | — |
| Vitamin C/Ascorbic acid | — | 3.00 | — | — |
| *Glycine soya* germ extract | — | — | 0.50 | — |
| *Arctium Lappa* root extract | — | — | — | 0.30 |
| *Pimpinella Anisum* fruit extract | 4.00 | — | — | — |
| Glycyrrhitic acid | — | 0.10 | — | — |
| N-Acetylhydroxyproline | — | — | 0.10 | — |
| Niacinamide | — | — | — | 0.20 |
| Magnesium ascorbylphosphate | 0.10 | — | — | — |
| Ellagic acid | — | 0.01 | — | — |
| Liquorice root extract | — | — | 0.10 | — |
| Seasalt | — | — | — | 0.05 |
| Isoserinol | 1.00 | — | — | — |
| Dihydroxypropyltrimonium chloride | — | 0.80 | — | — |
| N-(4-(2,4-Dihydroxy-phenyl)thiazol-2-yl)isobutyramide | 0.25 | 0.30 | 0.01 | 0.05 |
| Titanium dioxide | — | 1.00 | — | 1.00 |
| Bis-Ethylhexyloxyphenol Methoxyphenyl Triazine | 1.00 | 2.00 | 1.00 | 1.00 |
| Octocrylene | 1.00 | 1.00 | 2.00 | 2.00 |
| Butyl Methoxydibenzoylmethane | 2.00 | 2.00 | 1.00 | 2.00 |
| Ethylhexyl Salicylate | 1.00 | 1.00 | 2.00 | 1.00 |
| Citronellol | 0.05 | — | 0.05 | — |
| Coumarin | 0.05 | 0.05 | — | 0.05 |
| Triethyl citrate | — | — | 0.05 | 0.05 |
| Sodium hydroxide | q.s. | q.s. | q.s. | q.s. |
| Water | ad 100 | ad 100 | ad 100 | ad 100 |

| | Formulation examples | | | |
|---|---|---|---|---|
| Chemical name | 21 % by wt. | 22 % by wt. | 23 % by wt. | 24 % by wt. |
| Sucrose Polystearate + Hydrogenated Polyisobutene | 1.00 | 1.00 | 2.00 | 2.00 |
| Sodium stearoyl glutamate | 0.20 | 0.20 | 0.30 | 0.30 |
| C12-15 Alkyl benzoate | 1.50 | 1.50 | — | — |
| Cetyl alcohol | 0.50 | 0.50 | — | — |
| Cyclomethicone | 10.00 | 10.00 | 5.00 | 5.00 |
| Dimethicone | 3.00 | 3.00 | 2.50 | 2.50 |
| Glycerol | 7.50 | 7.50 | 5.00 | 5.00 |
| Isopropyl stearate | 1.00 | 1.00 | 2.00 | 2.00 |
| Paraffinum Liquidum (mineral oil) | 3.00 | 3.00 | 1.00 | 1.00 |
| Methylparaben | 0.10 | — | — | 0.10 |
| Ethylhexylglycerol | — | — | 0.30 | 0.10 |
| Propylparaben | 0.10 | — | — | — |
| Methylisothiazolinone | — | 0.05 | — | — |
| Phenoxyethanol | 0.40 | 0.50 | 0.40 | 0.40 |
| Potassium sorbate | 0.10 | 0.05 | 0.20 | 0.01 |
| Ascorbyl glucoside | 0.10 | — | — | — |
| Undecenoylphenylalanine | — | 0.50 | — | — |
| Kojic acid | — | — | 0.10 | — |
| Arbutin | — | — | — | 0.01 |
| Betaine | 0.20 | — | — | — |
| N-(4-(2,4-Dihydroxy-phenyl)thiazol-2-yl)isobutyramide | 0.10 | 0.10 | 0.05 | 0.05 |
| N-(4-(2,4-Dihydroxy-phenyl)thiazol-2-yl)pivalamide | 0.10 | 0.25 | 0.15 | 0.10 |
| N-(4-(2,4-Dihydroxy-phenyl)thiazol-2-yl)butyramide | 0.15 | 0.15 | 0.01 | 0.06 |
| Ethylhexyl methoxycinnamate | 1.00 | 2.00 | 1.00 | 1.00 |
| Butylmethoxydibenzoylmethane | 1.00 | 1.00 | 2.00 | 2.00 |
| Phenylbenzimidazolesulfonic acid | 2.00 | 2.00 | 1.00 | 2.00 |
| Acrylates/octylacrylamide copolymer | — | 1.00 | — | — |
| Butylene glycol | — | — | 3.00 | — |
| Polymethylsilsesquioxane | — | — | 1.00 | 1.00 |
| *Prunus Amygdalus Dulcis* Oil | — | — | 1.00 | — |
| Nylon-12 (1,8-Diazacyclo-tetradecane-2,7-dione Homopolymer) | — | 1.00 | 1.00 | — |
| Distarch phosphate | — | 1.00 | — | 1.00 |
| Methyl methacrylate crosspolymer | 1.00 | — | — | 1.00 |
| Aluminum starch octenylsuccinate | 1.00 | — | — | — |
| Ammonium Acryloyldimethyl-taurate/VP Copolymer | — | — | 0.25 | 0.25 |
| Xanthan gum | 0.10 | — | — | 0.10 |
| Acrylates/C10-30 Alkyl Acrylate Crosspolymer | 0.25 | 0.10 | — | — |
| Carbomer | — | 0.10 | 0.10 | — |
| Hexylcinnamal | 0.05 | 0.10 | — | 0.10 |
| 1-(1,2,3,4,5,6,7,8-octahydro-2,3,8,8,-tetramethyl-2-naphthyl)ethan-1-one | — | 0.10 | 0.10 | — |
| Linalool | — | — | 0.05 | 0.05 |
| Perfume | 0.20 | 0.20 | 0.20 | 0.20 |
| Sodium hydroxide | q.s. | q.s. | q.s. | q.s. |
| Water | ad 100 | ad 100 | ad 100 | ad 100 |

| | Formulation examples | | | |
|---|---|---|---|---|
| Chemical name | 25 % by wt. | 26 % by wt. | 27 % by wt. | 28 % by wt. |
| Sodium cetearyl sulfate | 0.15 | 0.15 | — | 0.15 |
| Glyceryl Stearate SE | 2.00 | 2.00 | — | 1.50 |
| Sodium Stearoyl Glutamate | — | — | 0.30 | — |
| C12-15 Alkyl benzoate | 2.50 | 2.50 | 2.50 | 2.50 |
| Octyldodecanol | 1.00 | 1.00 | — | — |
| Caprylic/capric triglyceride | 2.00 | 2.00 | 2.00 | 2.00 |
| Cetylstearyl alcohol | 2.00 | 2.00 | 3.00 | 1.00 |
| Cyclomethicone | 1.50 | 1.50 | 2.50 | 2.50 |
| Glyceryl Stearate | — | — | 2.00 | — |
| Dimethicone | 0.50 | 0.50 | 0.50 | 0.50 |
| Glycerol | 5.00 | 5.00 | 7.50 | 7.50 |
| Cetearyl alcohol | 1.00 | 1.50 | 1.00 | 1.00 |
| Isopropyl stearate | 3.00 | 3.00 | 2.00 | 2.00 |
| Paraffinum Liquidum (mineral oil) | 2.00 | 2.00 | 1.00 | 1.00 |
| Methylisothiazolinone | — | — | — | 0.05 |
| Phenoxyethanol | 0.40 | 0.50 | 0.40 | 0.30 |
| Methylparaben | 0.15 | — | — | — |
| Propylparaben | 0.10 | — | — | — |
| Piroctone olamine | — | 0.15 | — | — |
| Benzethonium chloride | — | — | 0.10 | — |
| Octanehydroxamic acid | 0.10 | 0.10 | — | 0.50 |
| Sodium benzoate | 0.05 | 0.20 | 0.10 | — |
| N-(4-(2,4-Dihydroxy-phenyl)thiazol-2-yl)isobutyramide | 0.10 | 0.10 | 0.05 | 0.05 |
| N-(4-(2,4-Dihydroxy-phenyl)thiazol-2-yl)pivalamide | 0.25 | 0.30 | 0.01 | 0.05 |
| N-(4-(2,4-Dihydroxy-phenyl)thiazol-2-yl)butyramide | 0.10 | 0.25 | 0.15 | 0.10 |
| N-(4-(2,4-Dihydroxy-phenyl)thiazol-2-yl)cyclohexanecarboxamide | 0.15 | 0.15 | 0.01 | 0.06 |
| Ethylhexylmethoxycinnamate | 1.00 | 2.00 | 1.00 | 1.00 |
| Butylmethoxydibenzoylmethane | 1.00 | 1.00 | 2.00 | 2.00 |
| Pentylene glycol | — | 1.00 | 1.00 | — |
| Butylene glycol | 1.00 | 1.50 | 3.00 | 3.00 |
| Dipropylene glycol | 0.50 | 1.00 | 0.80 | 0.10 |
| 2-Methyl-1,3-propanediol | — | — | — | — |
| 1,2-Hexanediol | — | — | — | 1.00 |
| Nylon-12 (1,8-Diazacyclo-tetradecane-2,7-dione Homopolymer) | 1.00 | 1.00 | 1.00 | 1.00 |
| Carbomer | — | — | 0.10 | 0.15 |
| Ammonium Acryloyldimethyl-taurate/VP Copolymer | 0.20 | — | — | — |
| *Chondrus Crispus* | 0.10 | 0.10 | — | — |
| Xanthan gum | — | — | 0.10 | — |
| Acrylates/C10-30 Alkyl Acrylate Crosspolymer | — | 0.20 | 0.10 | 0.10 |
| Coumarin | 0.10 | — | 0.05 | 0.05 |
| Hydroxyisohexyl 3-Cyclohexenecarboxaldehyde | 0.05 | 0.05 | 0.05 | 0.10 |

-continued

| Chemical/INCI name | | | | |
|---|---|---|---|---|
| 1-(1,2,3,4,5,6,7,8-octahydro-2,3,8,8,-tetramethyl-2-naphthyl)ethan-1-one | — | 0.05 | 0.10 | — |
| Perfume | 0.20 | 0.30 | 0.40 | 0.20 |
| Sodium hydroxide | q.s. | q.s. | q.s. | q.s. |
| Water | ad 100 | ad 100 | ad 100 | ad 100 |

| | Formulation examples | | | |
|---|---|---|---|---|
| Chemical/INCI name | 29 % by wt. | 30 % by wt. | 31 % by wt. | 32 % by wt. |
| Sodium cetearylsulfate | 0.15 | 0.15 | 0.20 | 0.20 |
| Glyceryl stearate, self-emulsifying | 2.00 | 2.00 | 1.50 | 1.50 |
| C12-15 Alkyl benzoate | 2.00 | 2.00 | 2.00 | 2.00 |
| Octyldodecanol | 1.00 | 1.00 | — | — |
| Caprylic/capric triglyceride | 2.00 | 2.00 | 2.00 | 2.00 |
| Cetylstearyl alcohol | 2.00 | 2.00 | 1.00 | 1.00 |
| Cyclomethicone | 1.00 | 1.00 | 2.00 | 2.00 |
| Dimethicone | 0.50 | 0.50 | 1.00 | 1.00 |
| Glycerol | 5.00 | 5.00 | 7.50 | 7.50 |
| Isopropyl palmitate | 2.50 | 2.50 | 2.00 | 2.00 |
| DMDM Hydantoin | 0.05 | 0.05 | 0.05 | 0.05 |
| Phenoxyethanol | 0.35 | 0.25 | 0.30 | 0.30 |
| Ethanol | — | — | 3.00 | 2.00 |
| Pentylene glycol | 1.00 | — | 1.00 | 1.50 |
| Potassium sorbate | 0.10 | 0.30 | — | 0.05 |
| Zingerone | 0.10 | — | — | — |
| Dihydromyricetin | — | 0.03 | — | — |
| White tea extract | — | — | 1.00 | — |
| 4-Hexylresorcinol | — | — | — | 0.30 |
| Phenylethylresorcinol | 0.50 | — | — | — |
| Ubiquinone | — | 0.10 | — | — |
| Cyanomethylphenylmenthane-carboxamide | — | — | 0.10 | — |
| Menthoxypropanediol | — | — | — | 0.10 |
| Menthanecarboxamide ethylpyridine | 0.10 | — | — | — |
| Hydroxyethylurea | — | 0.50 | — | — |
| Urea | — | — | 1.00 | — |
| N-(4-(2,4-Dihydroxy-phenyl)thiazol-2-yl)isobutyramide | 0.10 | 0.10 | 0.05 | 0.05 |
| Carbomer | 0.20 | 0.20 | 0.20 | 0.20 |
| Carrageenan | 0.10 | 0.10 | — | — |
| Xanthan gum | — | — | 0.20 | 0.20 |
| Acrylates/C10-30 Alkyl Acrylate Crosspolymer | — | — | — | 0.15 |
| Sodium Polyacrylate | — | 0.20 | — | — |
| Diethylhexyl 2,6-naphthalate | — | — | 1.00 | — |
| Phenylbenzimidazolesulfonic acid | 1.00 | 2.00 | 1.00 | 1.00 |
| Titanium dioxide | 1.00 | 1.00 | 2.00 | 2.00 |
| Diethylamino Hydroxybenzoyl Hexyl Benzoate | 2.00 | 2.00 | 1.00 | 2.00 |
| Octocrylene | 1.00 | 1.00 | 2.00 | 1.00 |
| 3,3,5-Trimethylcyclohexyl salicylate | — | 1.00 | — | — |
| Distarch phosphate | — | 1.00 | 1.00 | — |
| Methyl methacrylate crosspolymer | 1.00 | — | — | 1.00 |
| Polymethylsilsesquioxane | — | — | 1.00 | 1.00 |
| Acrylonitrile-methacrylonitrile-methyl-methacrylate Copolymer + Isopentane + Magnesium Hydroxide | 1.00 | 1.00 | — | — |
| 1-(1,2,3,4,5,6,7,8-octahydro-2,3,8,8,-tetramethyl-2-naphthyl)ethan-1-one | — | 0.10 | 0.10 | 0.05 |
| Hydroxyisohexyl 3-cyclo-hexenecarboxaldehyde | 0.05 | 0.05 | 0.10 | — |
| Linalyl acetate | 0.10 | — | 0.05 | 0.05 |
| Perfume | 0.15 | 0.15 | 0.30 | 0.30 |
| Sodium hydroxide | q.s. | q.s. | q.s. | q.s. |
| Water | ad 100 | ad 100 | ad 100 | ad 100 |

| | Formulation examples | | | |
|---|---|---|---|---|
| Chemical/INCI name | 33 % by wt. | 34 % by wt. | 35 % by wt. | 36 % by wt. |
| Sodium cetearylsulfate | 0.15 | 0.15 | 0.15 | 0.15 |
| Glyceryl stearate, self-emulsifying | 1.00 | 1.00 | 1.00 | 1.00 |
| C12-15 Alkyl benzoate | 2.00 | 2.50 | 2.00 | 2.00 |
| Isopropyl palmitate | 3.50 | 3.00 | 2.50 | 3.50 |
| Dimethicone | 1.00 | 1.00 | 1.00 | 1.0 |
| Cetylstearyl alcohol | 1.00 | 1.00 | 1.00 | 1.00 |
| Octyldodecyl Myristate | — | — | — | 1.00 |
| Butyrospermum Parkii Butter | — | — | 1.00 | — |
| Glycerol | 7.00 | 3.00 | 9.00 | 5.00 |
| Carbomer | 0.10 | 0.15 | 0.10 | 0.10 |
| Acrylates/C10-30 Alkyl Acrylate Crosspolymer | 0.15 | 0.10 | 0.10 | 0.15 |
| Xanthan gum | 0.15 | 0.15 | 0.15 | 0.15 |
| Phenylbenzimidazolesulfonic acid | 1.00 | 1.00 | 0.50 | 1.00 |
| Butylmethoxydibenzoylmethane | 1.50 | 1.50 | 1.50 | 1.50 |
| Ethylhexyl salicylate | 2.00 | 2.50 | 2.50 | 2.50 |
| Octocrylene | 1.50 | 1.50 | 2.50 | 1.50 |
| Titanium dioxide + trimethoxycaprylylsilane | 1.00 | — | 1.00 | — |
| Aluminum starch octenylsuccinate | — | 1.00 | — | 0.50 |
| Methyl methacrylate crosspolymer | 0.50 | — | 0.50 | — |
| Nylon-12 (1,8-Diazacyclo-tetradecane-2,7-dione Homopolymer) | 0.50 | — | 1.00 | — |
| Tapioca starch | 0.50 | 0.50 | — | 1.00 |
| Phenoxyethanol | 0.50 | 0.50 | 0.50 | 0.40 |
| Ethylhexylglycerol | 0.25 | — | 0.25 | — |
| 1,2-Hexanediol | — | 1.00 | — | 3.00 |
| Caprylyl glycol | — | 0.30 | 0.30 | — |
| 2-Methyl-1,2-propanediol | 2.00 | 2.00 | 2.00 | — |
| 1,3- Butanediol | 0.01 | — | 0.20 | — |
| Sodium benzoate | — | 0.10 | — | 0.20 |
| N-(4-(2,4-Dihydroxy-phenyl)thiazol-2-yl)isobutyramide | 0.10 | 0.10 | 0.05 | 0.05 |
| N-(4-(2,4-Dihydroxy-phenyl)thiazol-2-yl)pivalamide | 0.25 | 0.30 | 0.01 | 0.05 |
| Ethyllinalool | 0.05 | — | 0.05 | — |
| 3-Methyl-5-phenyl-1-pentanol | — | 0.05 | — | 0.05 |
| Geraniol | 0.05 | — | 0.05 | — |
| Sodium hydroxide | q.s. | q.s. | q.s. | q.s. |
| Water | ad 100 | ad 100 | ad 100 | ad 100 |

| | Formulation examples | | | |
|---|---|---|---|---|
| Chemical/INCI name | 37 % by wt. | 38 % by wt. | 39 % by wt. | 40 % by wt. |
| Polyglyceryl-10 stearate | 0.20 | 0.20 | 0.20 | 0.20 |
| Glyceryl stearate | 3.00 | 0.50 | 0.50 | 0.50 |
| C12-15 Alkyl benzoate | 4.00 | 2.00 | 1.50 | 2.50 |
| Isopropylpalmitate | 4.00 | 1.00 | 2.00 | 2.50 |
| Caprylic/capric triglyceride | 4.00 | 3.00 | 2.00 | 2.50 |
| Hydrogenated cocoglycerides | 3.00 | — | — | 2.00 |
| Butyrospermum Parkii Butter | 3.00 | — | 2.50 | — |
| Cetylstearyl alcohol | 5.00 | 3.50 | 4.00 | 3.00 |
| Paraffinum Liquidum (mineral oil) | — | — | — | 1.00 |
| Glycerol | 5.00 | 3.00 | 7.00 | 9.00 |
| Acrylates/C10-30 Alkyl Acrylate Crosspolymer | 0.30 | 0.20 | 0.15 | 0.20 |
| Methylisothiazolinone | 0.05 | — | — | 0.05 |
| Phenoxyethanol | 0.50 | 0.40 | 0.40 | 0.40 |
| Carbomer | 0.10 | 0.15 | 0.10 | 0.10 |
| Methylparaben | — | 0.10 | 0.10 | — |
| Propylparaben | — | 0.10 | — | — |
| Benzyl alcohol | 0.10 | 0.10 | 0.05 | 0.15 |
| Sodium benzoate | 0.50 | 0.40 | 0.40 | 0.40 |
| Nylon-12 (1,8-Diazacyclo-tetradecane-2,7-dione Homopolymer) | 1.00 | 0.50 | — | — |

| Chemical/INCI name | 37 % by wt. | 38 % by wt. | 39 % by wt. | 40 % by wt. |
|---|---|---|---|---|
| Polymethylsilsesquioxane | — | 1.00 | 0.50 | — |
| Methyl Methacrylate Crosspolymer | — | — | 1.00 | 0.50 |
| Tapioca starch | 0.50 | — | — | 0.50 |
| N-(4-(2,4-Dihydroxy-phenyl)thiazol-2-yl)isobutyramide | 0.10 | 0.10 | 0.05 | 0.05 |
| N-(4-(2,4-Dihydroxy-phenyl)thiazol-2-yl)pivalamide | 0.25 | 0.30 | 0.01 | 0.05 |
| N-(4-(2,4-Dihydroxy-phenyl)thiazol-2-yl)butyramide | 0.10 | 0.25 | 0.15 | 0.10 |
| N-(4-(2,4-Dihydroxy-phenyl)thiazol-2-yl)cyclohexanecarboxamide | 0.01 | 0.60 | 1.00 | 0.20 |
| Benzophenone-4 | 1.00 | 2.00 | 1.50 | 0.50 |
| Ethylhexyl Triazone | 2.00 | 0.50 | 1.00 | 2.00 |
| Ethanol | 3.00 | — | 2.00 | — |
| Geraniol | 0.05 | 0.05 | — | — |
| Benzyl salicylate | — | 0.05 | 0.05 | — |
| Ethyllinalool | — | — | 0.05 | 0.05 |
| Perfume | 0.20 | 0.15 | 0.30 | 0.30 |
| Sodium hydroxide | q.s. | q.s. | q.s. | q.s. |
| Water | ad 100 | ad 100 | ad 100 | ad 100 |

| Chemical/INCI name | 41 % by wt. | 42 % by wt. | 43 % by wt. | 44 % by wt. |
|---|---|---|---|---|
| Polyglyceryl-10 stearate | 0.20 | 0.20 | 0.15 | 0.15 |
| C12-15 Alkyl benzoate | 2.50 | 2.50 | 2.00 | 3.00 |
| Isopropyl palmitate | 2.50 | 2.50 | 2.00 | 2.00 |
| Caprylic/capric triglyceride | 2.00 | 2.50 | 1.00 | 2.00 |
| Glyceryl stearate | 1.00 | 1.00 | 0.50 | 0.50 |
| Octyldodecanol | 0.50 | — | — | 1.00 |
| Cyclomethicone | — | — | 0.50 | 0.50 |
| Butyl Methoxydibenzoylmethane | 1.00 | 2.00 | 2.00 | 1.00 |
| Octocrylene | 0.50 | 2.00 | 3.00 | 2.00 |
| Ethylhexyl salicylate | 2.00 | 1.00 | 1.00 | 1.50 |
| Phenylbenzimidazolesulfonic acid | 1.00 | 1.00 | 0.50 | 1.50 |
| Titanium dioxide | — | 1.00 | — | 1.00 |
| 3,3,5-Trimethylcyclohexyl salicylate | — | — | 1.00 | 1.00 |
| Glycerol | 9.00 | 5.00 | 7.00 | 7.00 |
| Tapioca starch | 1.00 | 1.00 | — | — |
| Acrylonitrile-methacrylonitrile-methyl-methacrylate Copolymer + Isopentane + Magnesium Hydroxide | — | — | 1.00 | 0.50 |
| Aluminum starch octenylsuccinate | — | — | 1.00 | 1.00 |
| Distarch phosphate | — | — | — | 1.00 |
| Methylisothiazolinone | 0.05 | 0.05 | — | — |
| Phenoxyethanol | 0.50 | 0.50 | 0.40 | 0.40 |
| Benzethonium chloride | — | — | — | 0.10 |
| Ethylhexylglycerol | — | — | 0.10 | — |
| Methylparaben | — | — | — | 0.20 |
| Salicylic acid | 0.01 | 0.05 | 0.10 | 0.02 |
| Potassium sorbate | 0.10 | 0.05 | 0.20 | 0.30 |
| Carbomer | 0.25 | 0.20 | 0.20 | 0.20 |
| Acrylates/C10-30 Alkyl Acrylate Crosspolymer | 0.20 | — | — | 0.15 |
| Ammonium Acryloyldimethyl-taurate/VP Copolymer | — | 0.25 | — | — |
| Sodium polyacrylate | — | — | 0.30 | — |
| Xanthan gum | — | — | — | 0.15 |
| N-(4-(2,4-Dihydroxy-phenyl)thiazol-2-yl)isobutyramide | 0.10 | 0.10 | 0.05 | 0.05 |
| Ethanol | 3.00 | 3.00 | — | — |
| Butylene glycol | — | — | 2.00 | 2.00 |
| Coumarin | — | 0.05 | 0.05 | — |
| Hexylcinnamal | 0.05 | 0.05 | — | 0.05 |
| Hexyl salicylate | — | — | 0.05 | 0.05 |
| Perfume | 0.15 | 0.20 | 0.25 | 0.30 |
| Sodium hydroxide | q.s. | q.s. | q.s. | q.s. |
| Water | ad 100 | ad 100 | ad 100 | ad 100 |

| Chemical/INCI name | 45 % by wt. | 46 % by wt. | 47 % by wt. | 48 % by wt. |
|---|---|---|---|---|
| Potassium cetylphosphate | 0.20 | 0.20 | 0.20 | 0.20 |
| Dicaprylyl carbonate | — | 1.00 | — | — |
| C12-15 Alkyl benzoate | 2.50 | 2.00 | 1.00 | 3.00 |
| Isopropyl palmitate | 2.50 | 2.00 | 3.00 | 1.00 |
| Caprylic/capric triglyceride | 2.50 | 2.00 | 1.50 | 2.00 |
| Cera Microcristallina | — | — | — | 0.50 |
| Cyclomethicone | 0.25 | — | 0.50 | 0.50 |
| Diethylhexyl 2,6-naphthalate | — | 0.50 | — | 1.00 |
| Diethylamino Hydroxybenzoyl Hexyl Benzoate | — | 1.00 | — | 1.00 |
| Ethylhexyl Salicylate | 1.00 | 0.50 | 2.00 | 1.00 |
| Octocrylene | 2.00 | 1.00 | 3.00 | 2.00 |
| Glycerol | 5.00 | 7.00 | 9.00 | 7.00 |
| Acrylates/C10-30 Alkyl Acrylate Crosspolymer | 0.10 | 0.30 | — | 0.10 |
| Sodium polyacrylate | 0.30 | — | — | — |
| Carbomer | — | 0.10 | 0.15 | 0.15 |
| Ammonium Acryloyldimethyl-taurate/VP Copolymer | — | — | 0.25 | — |
| *Chondrus Crispus* Extract (Carrageenan) | — | — | — | 0.10 |
| Methylisothiazolinone | 0.05 | 0.05 | — | — |
| Phenoxyethanol | 0.50 | 0.50 | 0.40 | 0.40 |
| Piroctone Olamine | — | — | — | 0.20 |
| Salicylic acid | 0.05 | 0.10 | 0.01 | 0.20 |
| Benzoic acid | 0.20 | 0.05 | 0.10 | 0.01 |
| Nylon-12 (1,8-Diazacyclo-tetradecane-2,7-dione Homopolymer) | 0.50 | — | 0.50 | 0.50 |
| Distarch phosphate | — | 1.00 | — | 0.50 |
| Methyl Methacrylate Crosspolymer | — | 0.50 | 0.50 | — |
| Caprylyl glycol | — | — | 0.30 | — |
| 1,2-Hexanediol | — | — | — | 0.50 |
| Butylene glycol | — | — | 2.00 | 2.00 |
| DMDM Hydantoin | — | — | 0.15 | — |
| *Glycyrrhiza Inflata* Root Extract (liquorice root) | — | — | 0.05 | — |
| N-(4-(2,4-Dihydroxy-phenyl)thiazol-2-yl)isobutyramide | 0.10 | 0.10 | 0.05 | 0.05 |
| N-(4-(2,4-Dihydroxy-phenyl)thiazol-2-yl)pivalamide | 0.25 | 0.30 | 0.01 | 0.05 |
| N-(4-(2,4-Dihydroxy-phenyl)thiazol-2-yl)butyramide | 0.10 | 0.25 | 0.15 | 0.10 |
| N-(4-(2,4-Dihydroxy-phenyl)thiazol-2-yl)cyclohexanecarboxamide | 0.01 | 0.60 | 1.00 | 0.20 |
| Hydroxyisohexyl 3-cyclo-hexenecarboxaldehyde | 0.05 | 0.05 | 0.05 | — |
| Citronellol | — | 0.05 | — | 0.05 |
| Benzyl salicylate | — | — | 0.05 | 0.05 |
| Perfume | 0.20 | 0.20 | 0.20 | 0.20 |
| Sodium hydroxide | q.s. | q.s. | q.s. | q.s. |
| Water | ad 100 | ad 100 | ad 100 | ad 100 |

| Chemical/INCI name | 49 % by wt. | 50 % by wt. | 51 % by wt. | 52 % by wt. |
|---|---|---|---|---|
| Potassium cetylphosphate | 0.20 | 0.20 | 0.25 | 0.20 |
| C12-15 Alkyl benzoate | 2.50 | 2.50 | 2.00 | 2.00 |
| Isopropyl palmitate | 2.50 | 2.50 | — | 3.00 |
| Isopropyl stearate | — | — | 2.00 | — |
| Caprylic/capric triglyceride | 2.50 | 2.50 | 1.50 | 2.00 |
| Glyceryl stearate | 1.00 | 1.00 | 1.25 | 1.50 |
| Octyldodecanol | — | — | 1.50 | — |
| Paraffinum Liquidum (mineral oil) | — | — | — | 1.00 |
| Glycerol | 5.00 | 7.00 | 9.00 | 6.00 |

-continued

| Chemical/INCI name | | | | |
|---|---|---|---|---|
| Bis-Ethylhexyloxyphenol Methoxyphenyl Triazines | — | 1.00 | — | 1.00 |
| Titanium dioxide + trimethoxycaprylylsilane | — | — | 1.00 | 1.00 |
| Phenylbenzimidazolesulfonic acid | 1.00 | 2.00 | 1.00 | 1.00 |
| Butylmethoxydibenzoylmethane | 1.00 | 1.00 | 2.00 | 2.00 |
| Disodiumphenyldibenzimidazole-tetrasulfonate | 2.00 | 2.00 | 1.00 | 2.00 |
| Ethylhexyltriazone | 1.00 | 1.00 | 2.00 | 1.00 |
| Ethylhexylmethoxycinnamate + BHT | 0.50 | 1.00 | 0.50 | 1.00 |
| Carbomer | — | 0.15 | 0.20 | 0.30 |
| Acrylates/C10-30 Alkyl Acrylate Crosspolymer | 0.30 | 0.10 | 0.15 | — |
| Xanthan gum | — | — | 0.15 | 0.10 |
| Methylisothiazolinone | 0.05 | — | — | — |
| Phenoxyethanol | 0.50 | 0.50 | 0.40 | 0.40 |
| Methylparaben | — | 0.10 | — | — |
| Ethylhexyl salicylate | — | — | 0.30 | — |
| Butylene glycol | — | — | 3.00 | 3.00 |
| Benzethonium chloride | — | — | — | 0.10 |
| Sodium benzoate | — | 0.20 | 0.05 | 0.10 |
| Propionic acid | 0.10 | 0.20 | 0.05 | 0.02 |
| Octanehydroxamic acid | 0.20 | 0.05 | 0.01 | 0.30 |
| N-(4-(2,4-Dihydroxy-phenyl)thiazol-2-yl)isobutyramide | 0.10 | 0.10 | 0.05 | 0.05 |
| N-(4-(2,4-Dihydroxy-phenyl)thiazol-2-yl)pivalamide | — | 0.30 | — | 0.05 |
| N-(4-(2,4-Dihydroxy-phenyl)thiazol-2-yl)butyramide | — | — | 0.15 | 0.10 |
| N-(4-(2,4-Dihydroxy-phenyl)thiazol-2-yl)cyclohexanecarboxamide | — | 0.60 | 1.00 | 0.20 |
| Coumarin | — | 0.05 | — | 0.05 |
| Linalool | 0.05 | — | — | 0.05 |
| Hexylcinnamal | 0.05 | 0.05 | — | — |
| 1-(1,2,3,4,5,6,7,8-octahydro-2,3,8,8,-tetramethyl-2-naphthyl)ethan-1-one | — | — | 0.10 | — |
| Perfume | 0.10 | 0.30 | 0.20 | 0.30 |
| BHT (tert-butylhydroxytoluene) | 0.05 | — | — | — |
| Tocopheryl acetate | — | 0.10 | — | — |
| Sodium hydroxide | q.s. | q.s. | q.s. | q.s. |
| Water | ad 100 | ad 100 | ad 100 | ad 100 |

W/O Emulsion

| | Formulation examples | |
|---|---|---|
| Chemical/INCI name | 53 % by wt. | 54 % by wt. |
| Polyglyceryl-3 diisostearate | 1.50 | 1.50 |
| PEG-40 Sorbitan Perisostearate | 2.50 | 2.50 |
| Lanolin alcohol | 0.50 | 0.50 |
| Paraffinum Liquidum (mineral oil) | 8.00 | 8.00 |
| Cera Microcrystallina | 2.50 | 2.50 |
| Cyclomethicone | 4.00 | 4.00 |
| Isohexadecane | 2.00 | 2.00 |
| Isopropyl palmitate | 5.00 | 5.00 |
| Iodopropynyl butylcarbamate | — | 0.10 |
| Magnesium sulfate | 0.5 | 0.50 |
| Potassium sorbate | 0.10 | 0.05 |
| Benzyl salicylate | 0.10 | 0.01 |
| 1,2-Octanediol | 0.01 | 0.05 |
| Sodium benzoate | 0.10 | 0.01 |
| Homosalate | 0.50 | 1.00 |
| Benzophenone-4 | 2.00 | 0.50 |
| N-(4-(2,4-Dihydroxyphenyl)thiazol-2-yl)isobutyramide | 0.10 | 0.10 |
| N-(4-(2,4-Dihydroxyphenyl)thiazol-2-yl)pivalamide | 0.25 | 0.05 |
| N-(4-(2,4-Dihydroxyphenyl)thiazol-2-yl)butyramide | 0.10 | 0.15 |
| N-(4-(2,4-Dihydroxyphenyl)thiazol-2-yl)cyclohexanecarboxamide | 0.01 | 0.02 |
| Glycerol | 7 | 7 |
| Perfume | q.s. | q.s. |
| Water | ad 100 | ad 100 |

Deodorant/Antiperspirant Example Formulations

| | Formulation examples | | | |
|---|---|---|---|---|
| Chemical/INCI name | 55 % by wt. | 56 % by wt. | 57 % by wt. | 58 % by wt. |
| Polyethylene glycol(21) stearyl ether | 2.50 | 2.50 | 1.50 | 1.50 |
| Polyethylene glycol(2) stearyl ether | 1.50 | 1.50 | 2.50 | 2.50 |
| Polypropylene glycol(15) stearyl ether | 3.00 | 3.00 | 4.00 | 4.00 |
| Trisodium salt of ethylenediaminetetraacetic acid (20% aqueous solution) | 1.50 | 1.50 | 1.50 | 1.50 |
| *Persea Gratissima* oil (avocado oil) | 0.10 | 0.10 | 0.15 | 0.15 |
| Perfume | q.s. | q.s. | q.s. | q.s. |
| 1-(1,2,3,4,5,6,7,8-octahydro-2,3,8,8,-tetramethyl-2-naphthyl)ethan-1-one | 0.10 | 0.05 | — | 0.05 |
| Linyl acetate | — | 0.05 | 0.05 | — |
| Citronellol | — | — | 0.05 | — |
| Triethyl citrate | — | — | — | 0.05 |
| Sodium benzoate | 0.10 | 0.02 | — | — |
| Potassium sorbate | — | — | 0.10 | 0.01 |
| Silver citrate | 0.10 | — | — | — |
| N-(4-(2,4-Dihydroxyphenyl)thiazol-2-yl)isobutyramide | 0.10 | 0.10 | 0.05 | 0.05 |
| N-(4-(2,4-Dihydroxyphenyl)thiazol-2-yl)pivalamide | 0.25 | — | — | 0.05 |
| N-(4-(2,4-Dihydroxyphenyl)thiazol-2-yl)butyramide | 0.10 | — | 0.15 | 0.10 |
| N-(4-(2,4-Dihydroxyphenyl)thiazol-2-yl)cyclohexanecarboxamide | 0.01 | — | — | — |
| Water, ad | ad 100 | ad 100 | ad 100 | ad 100 |

-continued

| Chemical/INCI name | Formulation examples | | | |
|---|---|---|---|---|
| | 59 % by wt. | 60 % by wt. | 61 % by wt. | 62 % by wt. |
| Isoceteth-20 | 3.50 | 3.00 | 4.00 | 4.00 |
| Glyceryl isostearate | 2.00 | 2.00 | 2.00 | 2.50 |
| Dicaprylyl ether | — | 0.50 | 2.00 | 2.50 |
| Caprylic/capric acid ester | 2.00 | 1.50 | — | — |
| Aluminum chlorohydrate | 5.00 | 5.00 | — | 3.00 |
| Persea Gratissima oil (avocado oil) | — | — | 0.20 | — |
| Polyethylene glycol(150) distearate | 0.50 | 0.50 | 1.00 | 1.00 |
| Glycerol | 4.00 | 2.00 | — | 2.00 |
| Butylene glycol | — | 3.00 | 1.00 | 2.00 |
| Propylene glycol | 3.00 | — | 3.00 | — |
| 4-[(Cyclopentylhydroxyphenylacetyl)oxy]-1,1-dimethylpiperidinium bromide | 0.05 | 0.10 | — | — |
| N-(4-(2,4-Dihydroxyphenyl)thiazol-2-yl)isobutyramide | 0.10 | 0.10 | 0.05 | 0.05 |
| N-(4-(2,4-Dihydroxyphenyl)thiazol-2-yl)pivalamide | — | — | — | 0.05 |
| N-(4-(2,4-Dihydroxyphenyl)thiazol-2-yl)butyramide | — | — | 0.15 | — |
| N-(4-(2,4-Dihydroxyphenyl)thiazol-2-yl)cyclohexanecarboxamide | — | — | 1.00 | 0.20 |
| Sodium benzoate | 0.10 | 0.02 | — | — |
| Potassium sorbate | — | — | 0.10 | 0.01 |
| Geraniol | — | 0.05 | — | — |
| Ethyllinalool | — | — | 0.05 | — |
| Linalool | — | — | — | 0.10 |
| Perfume | 0.25 | 0.50 | 0.50 | 0.75 |
| Water, ad | ad 100 | ad 100 | ad 100 | ad 100 |

| Chemical/INCI name | Formulation examples | | | |
|---|---|---|---|---|
| | 63 % by wt. | 64 % by wt. | 65 % by wt. | 66 % by wt. |
| Polyoxyethylene(20) cetylstearyl ether | 3.00 | 3.00 | 4.00 | 4.00 |
| Polyoxyethylene(12) cetylstearyl ether | 0.50 | 0.50 | — | — |
| Glycerol stearate | 3.00 | 3.00 | 3.00 | 3.00 |
| Cetylstearyl alcohol | 0.50 | 0.50 | — | — |
| Cetyl palmitate | 0.50 | 0.50 | — | — |
| Caprylic/capric acid ester | 4.00 | 4.00 | 3.50 | 3.50 |
| Di-n-octyl ether | 5.00 | 5.00 | 5.00 | 5.00 |
| Polyethylene glycol(150) distearate | — | — | 1.00 | 1.00 |
| Glycerol | 4.00 | 4.00 | 2.00 | 2.00 |
| N-(4-(2,4-Dihydroxyphenyl)thiazol-2-yl)isobutyramide | 0.10 | 0.10 | 0.05 | 0.05 |
| N-(4-(2,4-Dihydroxyphenyl)thiazol-2-yl)pivalamide | 0.25 | 0.30 | 0.01 | — |
| N-(4-(2,4-Dihydroxyphenyl)thiazol-2-yl)butyramide | 0.10 | 0.25 | 0.15 | — |
| N-(4-(2,4-Dihydroxyphenyl)thiazol-2-yl)cyclohexanecarboxamide | 0.01 | 0.60 | 1.00 | — |
| 1,3-Butanediol | 0.10 | — | 0.10 | — |
| Sorbic acid | 0.20 | 0.01 | 0.02 | 0.02 |
| Hexylcinnamal | 0.05 | 0.10 | — | — |
| 1-(1,2,3,4,5,6,7,8-octahydro-2,3,8,8,-tetramethyl-2-naphthyl)ethan-1-one | — | 0.05 | 0.10 | — |
| 3-Methyl-5-phenyl-1-pentanol | 0.05 | — | — | 0.05 |
| Perfume | 0.30 | 0.30 | 0.50 | 0.50 |
| Water, ad | ad 100.00 | ad 100.00 | ad 100.00 | ad 100.00 |

| Chemical/INCI name | Formulation examples | | | |
|---|---|---|---|---|
| | 67 % by wt. | 68 % by wt. | 69 % by wt. | 70 % by wt. |
| Steareth-100 | 1.00 | 1.00 | 1.00 | 1.00 |
| Polyglyceryl-3 diisostearate | 1.60 | 1.60 | 1.60 | 1.60 |
| PEG-45/Dodecyl glycol copolymer | 0.80 | 0.80 | 0.80 | 0.80 |
| C20-40 alkyl stearate | 10.00 | 10.00 | 10.00 | 10.00 |
| Caprylic/capric triglyceride | 3.00 | 3.00 | 3.00 | 3.00 |
| Octyldodecanol | 3.00 | 3.00 | 3.00 | 3.00 |
| Dicaprylyl ether | 4.00 | 4.00 | 4.00 | 4.00 |
| Potassium sorbate | 0.10 | 0.10 | 0.10 | 0.10 |
| Ethylhexylglycerol | 0.10 | 0.10 | 0.10 | 0.10 |
| Butylene glycol | 4.00 | 4.00 | 4.00 | 4.00 |

-continued

| | | | | |
|---|---|---|---|---|
| N-(4-(2,4-Dihydroxyphenyl)thiazol-2-yl)isobutyramide | 0.10 | 0.10 | 0.05 | 0.05 |
| N-(4-(2,4-Dihydroxyphenyl)thiazol-2-yl)pivalamide | 0.25 | 0.30 | — | 0.05 |
| N-(4-(2,4-Dihydroxyphenyl)thiazol-2-yl)butyramide | 0.10 | 0.25 | — | 0.10 |
| N-(4-(2,4-Dihydroxyphenyl)thiazol-2-yl)cyclohexanecarboxamide | 0.01 | 0.60 | — | 0.20 |
| Hydroxyisohexyl 3-cyclohexenecarboxaldehyde | 0.05 | 0.05 | 0.05 | 0.05 |
| Perfume | 0.35 | 0.30 | 0.25 | 0.15 |
| Water, ad | ad 100.00 | ad 100.00 | ad 100.00 | ad 100.00 |

Example Formulations

| | Formulation examples | | | |
|---|---|---|---|---|
| Chemical/INCI name | 71 % by wt. | 72 % by wt. | 73 % by wt. | 74 % by wt. |
| Alcohol denat. | 20.0 | 20.0 | 30.0 | 30.0 |
| Hydroxyethylcellulose | 0.40 | 0.40 | 0.30 | 0.30 |
| Polyethylene glycol 400 | 3.00 | 3.00 | 2.00 | 2.00 |
| Polyethylene glycol (2000) hydrogenated castor oil | 2.00 | 2.00 | 3.00 | 3.00 |
| *Persea Gratissima* oil (avocado oil) | 0.50 | 0.50 | 0.10 | 0.10 |
| 4-[(Cyclopentylhydroxyphenylacetyl)oxy]-1,1-dimethylpiperidinium bromide | 0.10 | 0.30 | — | — |
| Sodium benzoate | 0.01 | 0.02 | 0.01 | 0.02 |
| DMDM Hydantoin | 0.02 | 0.01 | 0.02 | 0.01 |
| N-(4-(2,4-Dihydroxyphenyl)thiazol-2-yl)isobutyramide | 0.10 | 0.10 | 0.05 | 0.01 |
| N-(4-(2,4-Dihydroxyphenyl)thiazol-2-yl)pivalamide | 0.25 | — | 0.01 | 0.05 |
| N-(4-(2,4-Dihydroxyphenyl)thiazol-2-yl)butyramide | 0.10 | — | 0.15 | — |
| N-(4-(2,4-Dihydroxyphenyl)thiazol-2-yl)cyclohexanecarboxamide | 0.01 | — | 1.00 | 0.20 |
| Coumarin | — | — | 0.05 | — |
| Benzyl salicylate | — | 0.05 | — | — |
| Butylphenylmethylpropional | 0.05 | — | — | — |
| Perfume | 0.25 | 0.30 | 0.50 | 0.30 |
| Water, ad | ad 100 | ad 100 | ad 100 | ad 100 |

| | Formulation examples | | | |
|---|---|---|---|---|
| Chemical/INCI name | 75 % by wt. | 76 % by wt. | 77 % by wt. | 78 % by wt. |
| 2-Octyldodecanol | 0.50 | 0.50 | 0.50 | 0.50 |
| 1,2-Propylene glycol | 1.00 | 1.00 | 1.00 | 1.00 |
| 2-Butyloctanoic acid | 0.25 | — | 0.25 | — |
| Aluminum chlorohydrate | 2.00 | 3.00 | — | 3.00 |
| N-(4-(2,4-Dihydroxyphenyl)thiazol-2-yl)isobutyramide | 0.10 | — | 0.10 | 0.05 |
| N-(4-(2,4-Dihydroxyphenyl)thiazol-2-yl)pivalamide | 0.25 | 0.30 | 0.01 | — |
| N-(4-(2,4-Dihydroxyphenyl)thiazol-2-yl)butyramide | 0.10 | 0.25 | 0.15 | — |
| N-(4-(2,4-Dihydroxyphenyl)thiazol-2-yl)cyclohexanecarboxamide | 0.01 | 0.60 | 1.00 | — |
| Sorbic acid | 0.10 | 0.10 | 0.10 | 0.10 |
| Sodium benzoate | 0.10 | 0.10 | 0.10 | 0.10 |
| Linalool | 0.05 | — | 0.05 | 0.05 |
| Coumarin | — | — | 0.05 | — |
| Benzyl salicylate | 0.05 | 0.05 | — | 0.05 |
| Perfume | 0.10 | 0.20 | 0.40 | 0.20 |
| Ethanol | ad 100 | ad 100 | ad 100 | ad 100 |

The liquid phase obtained by mixing together the respective constituents is poured into aerosol containers with a propane/butane mixture (2.7) in the ratio 39:61.

| | Formulation examples | | |
|---|---|---|---|
| Chemical name | 79 % by wt. | 80 % by wt. | 81 % by wt. |
| Alcohol denat. | 20.0 | 30.0 | 20.0 |
| Hydroxyethylcellulose | 0.40 | 0.30 | 0.40 |
| Polyethylene glycol 400 | 3.00 | 2.00 | 3.00 |
| Polyethylene glycol (2000) hydrogenated castor oil | 2.00 | 3.00 | 2.00 |
| Persea Gratissima oil (avocado oil) | 0.50 | 0.10 | 0.50 |
| 4-[(Cyclopentylhydroxyphenylacetyl)oxy]-1,1-dimethyl-piperidinium bromide | 0.05 | — | — |
| N-(4-(2,4-Dihydroxyphenyl)thiazol-2-yl)isobutyramide | 0.10 | 0.10 | 0.05 |
| N-(4-(2,4-Dihydroxyphenyl)thiazol-2-yl)pivalamide | — | 0.30 | 0.01 |
| N-(4-(2,4-Dihydroxyphenyl)thiazol-2-yl)butyramide | — | 0.25 | 0.15 |
| N-(4-(2,4-Dihydroxyphenyl)thiazol-2-yl)cyclohexanecarboxamide | — | 0.60 | 1.00 |
| Potassium sorbate | 0.20 | 0.10 | 0.01 |
| Octanehydroxamic acid | 0.01 | 0.20 | 0.10 |
| 2-Butyloctanoic acid | — | 0.10 | — |
| Geraniol | — | 0.05 | — |
| Citronellol | 0.05 | — | — |
| Ethyllinalool | — | — | 0.05 |
| Perfume | 0.30 | 0.40 | 0.20 |
| Water, ad | ad 100 | ad 100 | ad 100 |

| | Formulation examples | | |
|---|---|---|---|
| Chemical name | 82 % by wt. | 83 % by wt. | 84 % by wt. |
| Glycerol monostearate | 5.00 | 5.00 | 5.00 |
| Polyethylene glycol (2000) monostearate | 2.00 | 2.00 | 2.00 |
| Stearyl alcohol | 3.00 | 3.00 | 3.00 |
| Cyclomethicone | 4.00 | 4.00 | 4.00 |
| Paraffin oil | 6.00 | 6.00 | 6.00 |
| Trisodium EDTA | 0.20 | 0.20 | 0.20 |
| Aluminum chlorohydrate | 2.50 | 2.50 | 2.50 |
| N-(4-(2,4-Dihydroxyphenyl)thiazol-2-yl)isobutyramide | 0.10 | 0.10 | 0.05 |
| N-(4-(2,4-Dihydroxyphenyl)thiazol-2-yl)pivalamide | 0.25 | — | 0.01 |
| N-(4-(2,4-Dihydroxyphenyl)thiazol-2-yl)butyramide | 0.10 | — | 0.15 |
| N-(4-(2,4-Dihydroxyphenyl)thiazol-2-yl)cyclohexanecarboxamide | 0.01 | — | 1.00 |
| Sodium benzoate | 0.20 | 0.10 | 0.10 |
| Methylpropanediol | 0.01 | 0.50 | 0.60 |
| 2-Methylpropanediol | 3.00 | 3.00 | 3.00 |
| 2-Ethylhexyl glycerol ether | 0.50 | 0.50 | 0.50 |
| Benzyl salicylate | — | — | 0.05 |
| Triethyl citrate | — | 0.05 | — |
| Hexylcinnamal | 0.05 | — | — |
| Perfume | 0.40 | 0.30 | 0.20 |
| Water, ad | 100 | 100 | 100 |

Hair Shampoo

| | Example formulation | |
|---|---|---|
| Chemical name | 85 % by wt. | 86 % by wt. |
| Cocamidopropylbetaine | 2.50 | 2.50 |
| Sodium laureth sulfate | 9.00 | 9.00 |
| PEG-40 hydrogenated castor oil | 0.50 | 0.50 |
| Polyquaternium-10 | 0.20 | 0.20 |
| PEG-8 | 0.50 | 0.10 |
| Sodium benzoate | 0.45 | 0.45 |
| Laureth-9 | 2.20 | 2.20 |
| Sodium salicylate | 0.20 | 0.20 |
| Epsilon-poly-L-lysine | — | 0.25 |
| Climbazole | 0.45 | 0.45 |
| Pearlescence | 1.50 | 1.50 |
| Butyl Acrylate/ethyltrimonium chloride methacrylate/styrene copolymer | 2.50 | 1.00 |
| N-(4-(2,4-Dihydroxyphenyl)thiazol-2-yl)isobutyramide | 0.10 | 0.10 |
| N-(4-(2,4-Dihydroxyphenyl)thiazol-2-yl)pivalamide | 0.25 | — |
| N-(4-(2,4-Dihydroxyphenyl)thiazol-2-yl)butyramide | 0.10 | — |
| N-(4-(2,4-Dihydroxyphenyl)thiazol-2-yl)cyclohexanecarboxamide | 0.01 | — |
| Sodium benzoate | 0.10 | 0.15 |
| Perfume | 0.30 | 0.30 |
| Citric acid | q.s. | q.s. |
| Sodium chloride | q.s. | q.s. |
| Water | ad 100 | ad 100 |

Antidandruff Shampoo

|  | Example formulation | |
|---|---|---|
|  | 87 | 88 |
| Chemical name | % by wt. | % by wt. |
| Sodium lauryl ether sulfate | 9.00 | 10.00 |
| Cocamidopropylbetaine | 4.00 | 3.00 |
| Disodium PEG-5 lauryl citrate sulfosuccinate | — | 1.00 |
| Thickener | 0.20 | 0.40 |
| Polyquaternium-10 | 0.30 | 0.10 |
| Guar hydroxypropyltrimonium chloride | 0.20 | — |
| Potassium sorbate | 0.10 | 0.20 |
| Climbazole | — | 0.50 |
| Epsilon-poly-L-lysine | 1.00 | 0.20 |
| Laureth-9 | — | 2.00 |
| Piroctone olamine | 1.00 | 0.50 |
| Selenium sulfide | 0.20 | — |
| Zinc pyrithione | 1.00 | 1.00 |
| Pearlescence | — | 2.50 |
| Opacifier | — | 0.50 |
| PEG-40 hydrogenated castor oil | 0.50 | 0.20 |
| N-(4-(2,4-Dihydroxyphenyl)thiazol-2-yl)isobutyramide | 0.10 | 0.10 |
| N-(4-(2,4-Dihydroxyphenyl)thiazol-2-yl)pivalamide | 0.25 | — |
| N-(4-(2,4-Dihydroxyphenyl)thiazol-2-yl)butyramide | 0.10 | — |
| N-(4-(2,4-Dihydroxyphenyl)thiazol-2-yl)cyclohexanecarboxamide | 0.01 | — |
| Sodium salicylate | 0.30 | 0.20 |
| Sodium benzoate | 0.25 | 0.30 |
| Sodium chloride | q.s. | q.s. |
| Citric acid | q.s. | q.s. |
| Perfume | q.s. | q.s. |
| Water | ad 100 | ad 100 |

Hair Tonic

|  | Example formulation | |
|---|---|---|
|  | 89 | 90 |
| Chemical name | % by wt. | % by wt. |
| Ethanol | 30.00 | 40.00 |
| Panthenol | 0.20 | 0.10 |
| Tocopheryl acetate | 0.20 | — |
| Pentylene glycol | 0.10 | 0.15 |
| C12-13 Alkyl lactate | 0.20 | 0.10 |
| N-(4-(2,4-Dihydroxyphenyl)thiazol-2-yl)isobutyramide | 0.10 | 0.10 |
| N-(4-(2,4-Dihydroxyphenyl)thiazol-2-yl)pivalamide | 0.25 | — |
| N-(4-(2,4-Dihydroxyphenyl)thiazol-2-yl)butyramide | 0.10 | — |
| N-(4-(2,4-Dihydroxyphenyl)thiazol-2-yl)cyclohexanecarboxamide | 0.01 | — |
| Climbazole | 0.1 | 0.1 |
| PEG-40 hydrogenated castor oil | — | 0.3 |
| Perfume, preservative | q.s. | q.s. |
| Water | ad 100 | ad 100 |

What is claimed is:

1. An active ingredient combination of one or more alkylamidothiazoles and one or more cosmetically or dermatologically acceptable preservatives, wherein the one or more alkylamidothiazoles comprise at least one compound of formula

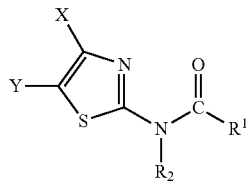

in which $R^1$, $R_2$, X and Y are different, partly identical or completely identical and, independently of one another, represent:

$R^1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alkyl-morpholine, —$C_1$-$C_{24}$ alkyl-piperidine, —$C_1$-$C_{24}$ alkyl-piperazino, —$C_1$-$C_{24}$ alkyl-piperazino-N-alkyl;

$R_2$=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-hydroxyalkyl (linear and branched), —$C_1$-$C_{24}$-alkylaryl (linear and branched), —$C_1$-$C_{24}$-alkylheteroaryl (linear and branched);

X=mono- or polysubstituted phenyl;

Y=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cycloalkyl, —COO-aryl, —COO-heteroaryl;

and wherein the one or more alkylamidothiazoles are present as free base and/or as cosmetically and dermatologically acceptable salt thereof.

2. The active ingredient combination of claim 1, wherein X represents 2,4-dihydroxyphenyl, 2,3-dihydroxyphenyl, 2,4-dimethoxyphenyl, or 2,3-dimethoxyphenyl.

3. The active ingredient combination of claim 1, wherein the one or more alkylamidothiazoles comprise one or more alkylamidothiazoles of formula

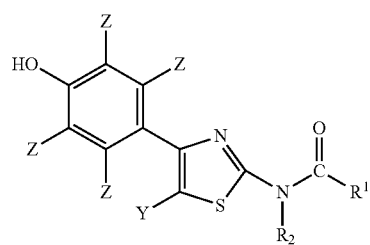

in which the substituents Z independently represent —H, —OH, —F, —Cl, —Br, —I, -OMe, —$NH_2$, —CN, acetyl.

4. The active ingredient combination of claim 3, wherein the one or more alkylamidothiazoles comprise one or more alkylamidothiazoles of formula

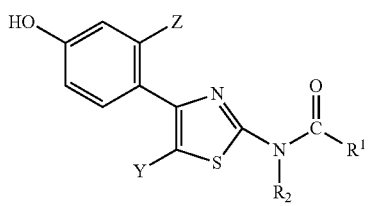

in which the substituent Z represents —H, —OH, —F, —Cl, —Br, —I, -OMe, —NH$_2$, —CN.

5. The active ingredient combination of claim 1, wherein the combination comprises one or more alkylamidothiazoles of formula

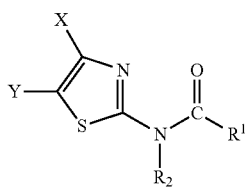

in which

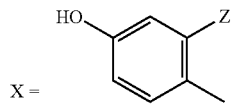

Y=H;

R$^1$=—C$_1$-C$_{24}$-alkyl (linear and branched), —C$_1$-C$_{24}$-alkenyl (linear and branched), —C$_1$-C$_8$-cycloalkyl, —C$_1$-C$_8$-cycloalkyl-alkylhydroxy, —C$_1$-C$_{24}$ alkylhydroxy (linear and branched), —C$_1$-C$_{24}$ alkylamine (linear and branched), —C$_1$-C$_{24}$-alkylaryl (linear and branched), —C$_1$-C$_{24}$-alkylaryl-alkyl-hydroxy (linear and branched), —C$_1$-C$_{24}$-alkylheteroaryl (linear and branched), —C$_1$-C$_{24}$-alkyl-O—C$_1$-C$_{24}$-alkyl (linear and branched), —C$_1$-C$_{24}$-alkyl-morpholino, —C$_1$-C$_{24}$ alkyl-piperidine, —C$_1$-C$_{24}$ alkyl-piperazine, —C$_1$-C$_{24}$ alky-piperazino-N-alkyl;

R$_2$=H, —C$_1$-C$_{24}$-alkyl (linear and branched);

Z=—H, —OH, —F, —Cl, —Br, —I, -OMe, —NH$_2$, —CN, acetyl.

6. The active ingredient combination of claim 1, wherein the combination comprises one or more alkylamidothiazoles of formula

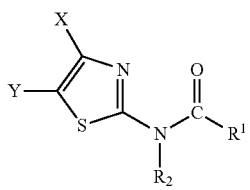

in which

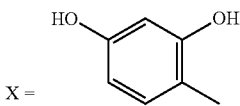

Y=H;

R$^1$=—C$_1$-C$_{24}$-alkyl (linear and branched), —C$_1$-C$_{24}$-alkenyl (linear and branched), —C$_1$-C$_8$-cycloalkyl, —C$_1$-C$_8$-cycloalkyl-alkylhydroxy, —C$_1$-C$_{24}$-alkylhydroxy (linear and branched), —C$_1$-C$_{24}$ alkylamine (linear and branched), —C$_1$-C$_{24}$-alkylaryl (linear and branched), —C$_1$-C$_{24}$-alkyl-aryl-alkyl-hydroxy (linear and branched), —C$_1$-C$_{24}$-alkylheteroaryl (linear and branched), —C$_1$-C$_{24}$-alkyl-O—C$_1$-C$_{24}$-alkyl (linear and branched), —C$_1$-C$_{24}$ alkyl-morpholine, —C$_1$-C$_{24}$ alkyl-piperidine, —C$_1$-C$_{24}$ alkyl-piperazine, —C$_1$-C$_{24}$ alkyl-piperazino-N-alkyl;

R$_2$=H.

7. The active ingredient combination of claim 1, wherein the combination comprises one or more of the following alkylamidothiazoles:

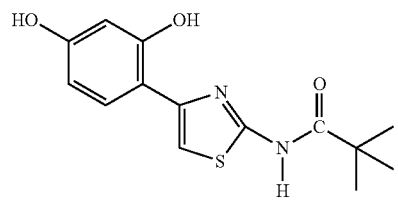 [SMILES: CC(C)(C)C(=O)Nc1nc(-c2ccc(O)cc2O)cs1]

N-(4-(2,4-dihydroxyphenyl)thiazol-2-yl)pivalamide

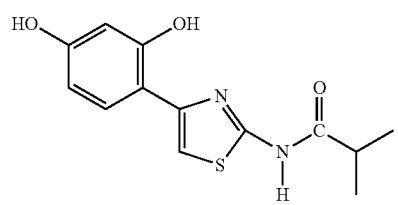 [SMILES: CC(C)C(=O)Nc1nc(-c2ccc(O)cc2O)cs1]

N-(4-(2,4-dihydroxyphenyl)thiazol-2-yl)isobutyramide

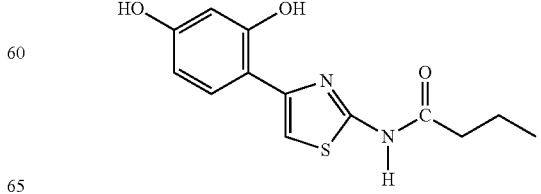

N-(4-(2,4-dihydroxyphenyl)thiazol-2-yl)butyramide

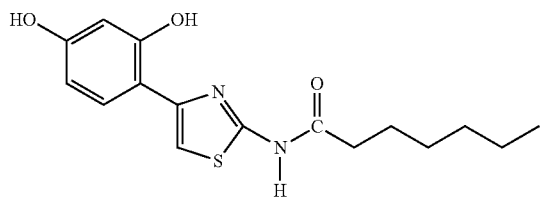 [SMILES: CCCCCCC(=O)Nc1nc(-c2ccc(O)cc2O)cs1]

N-(4-(2,4-dihydroxyphenyl)thiazol-2-yl)heptanamide

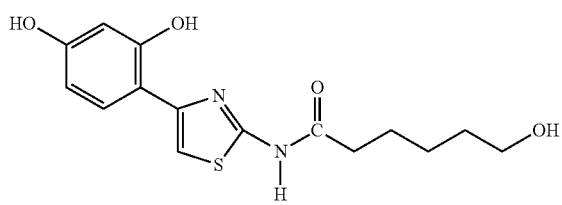 [SMILES: O=C(CCCCCO)Nc1nc(-c2ccc(O)cc2O)cs1]

N-(4-(2,4-dihydroxyphenyl)thiazol-2-yl)-6-hydroxy-hexanamide

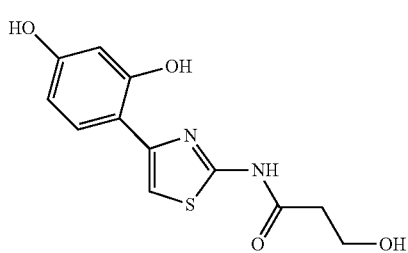 [SMILES: O=C(CCO)Nc1nc(-c2ccc(O)cc2O)cs1]

N-(4-(2,4-dihydroxyphenyl)thiazol-2-yl)-3-hydroxypropanamide

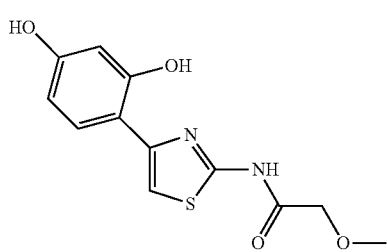 [SMILES: COCC(=O)Nc1nc(-c2ccc(O)cc2O)cs1]

N-(4-(2,4-dihydroxyphenyl)thiazol-2-yl)-2-methoxyacetamide

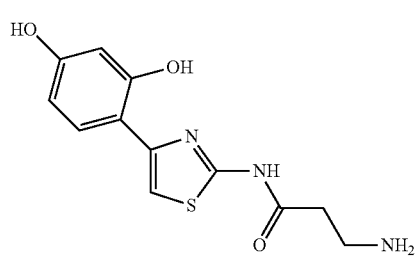 [SMILES: NCCC(=O)Nc1nc(-c2ccc(O)cc2O)cs1]

3-amino-N-(4-(2,4-dihydroxyphenyl)thiazol-2-yl)propanamide

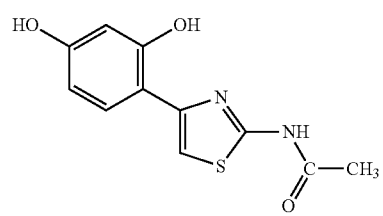 [SMILES: CC(=O)Nc1nc(-c2ccc(O)cc2O)cs1]

N-(4-(2,4-dihydroxyphenyl)thiazol-2-yl)acetamide

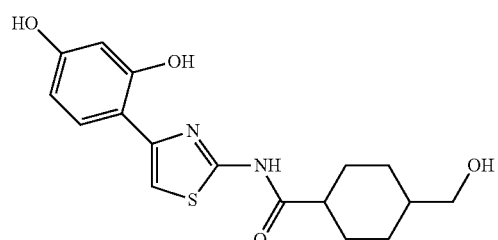

N-(4-(2,4-dihydroxyphenyl)thiazol-2-yl)-4-(hydroxymethyl)cyclohexanecarboxamide

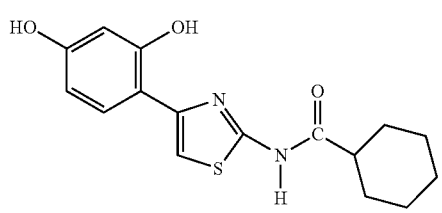 [SMILES: O=C(Nc1nc(-c2ccc(O)cc2O)cs1)C1CCCCC1]

N-(4-(2,4-dihydroxyphenyl)thiazol-2-yl)cyclohexanecarboxamide and

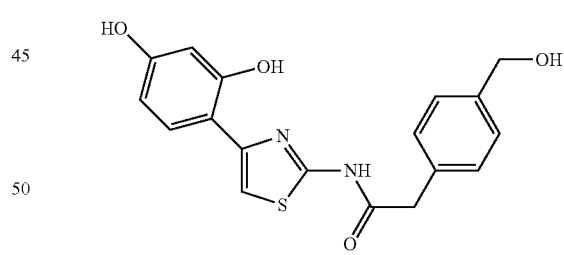

N-(4-(2,4-dihydroxyphenyl)thiazol-2-yl)-2-(4-(hydroxymethyl)phenyl)acetamide.

8. The active ingredient combination of claim 1, wherein the combination comprises one or more alkylamidothiazoles in the form of a cosmetically and dermatologically acceptable salt, which salt is selected from one or more of a halide, a carbonate, an ascorbate, a sulfate, an acetate, a phosphate.

9. The active ingredient combination of claim 1, wherein the one or more preservatives comprise one or more of ethylparaben, propylparaben, methylisothiazolinone, methylpropanediol, butylene glycol, propylene glycol, ethylhexylglycerol, sodium benzoate, 1,2-hexanediol, 1,3-butanediol, 1,2-octanediol, potassium sorbate, 1,3-dimethylol-5,5- dimethyl hydantoin, benzyl alcohol, phenoxyethanol, dehydroacetic acid, piroctone olamine, methylparaben, alcohol, octanehydroxamic acid, benzethonium chloride, glyceryl caprylate, pentylene glycol, lauroyl ethyl arginate, salicylic acid, benzoic acid, propionic acid, sorbic acid.

10. The active ingredient combination of claim 1, wherein the one or more preservatives comprise one or more of salicylic acid, benzoic acid, dehydroacetic acid, as such and/or in the form of physiologically acceptable water-soluble metal salts thereof.

11. The active ingredient combination of claim 1, wherein the one or more preservatives comprise one or more of methylisothiazolinone, potassium sorbate, sodium benzoate, ethylhexylglycerol, benzyl alcohol, benzethonium chloride.

12. The active ingredient combination of claim 1, wherein the one or more preservatives comprise ethylhexylglycerol.

13. The active ingredient combination of claim 1, wherein the combination comprises more than one alkylamidothiazole.

14. The active ingredient combination of claim 1, wherein the one or more alkylamidothiazoles comprise N-(4-(2,4-dihydroxyphenyl)thiazol-2-yl)pivalamide.

15. The active ingredient combination of claim 1, wherein the one or more alkylamidothiazoles comprise N-(4-(2,4-dihydroxyphenyl)thiazol-2-yl)isobutyramide.

16. The active ingredient combination of claim 1, wherein the one or more alkylamidothiazoles comprise N-(4-(2,4-dihydroxyphenyl)thiazol-2-yl)butyramide.

17. The active ingredient combination of claim 1, wherein the one or more alkylamidothiazoles comprise N-(4-(2,4-dihydroxyphenyl)thiazol-2-yl)cyclohexanecarboxamide.

18. The active ingredient combination of claim 14, wherein the one or more preservatives comprise ethylhexylglycerol.

19. The active ingredient combination of claim 15, wherein the one or more preservatives comprise ethylhexylglycerol.

20. The active ingredient combination of claim 16, wherein the one or more preservatives comprise ethylhexylglycerol.

* * * * *